US009279000B2

(12) United States Patent
Sun et al.

(10) Patent No.: US 9,279,000 B2
(45) Date of Patent: *Mar. 8, 2016

(54) HIGH-CELL DENSITY FED-BATCH FERMENTATION PROCESS FOR PRODUCING RECOMBINANT PROTEIN

(71) Applicant: Wyeth LLC, Madison, NJ (US)

(72) Inventors: Wei-Qiang Willie Sun, Morristown, NJ (US); Earl Joseph Pursell, Valley Cottage, NY (US)

(73) Assignee: Wyeth LLC, New York, NY (US)

( * ) Notice: Subject to any disclaimer, the term of this patent is extended or adjusted under 35 U.S.C. 154(b) by 50 days.

This patent is subject to a terminal disclaimer.

(21) Appl. No.: 14/135,434

(22) Filed: Dec. 19, 2013

(65) Prior Publication Data

US 2014/0113329 A1    Apr. 24, 2014

Related U.S. Application Data

(63) Continuation of application No. 11/829,703, filed on Jul. 27, 2007, now Pat. No. 8,632,995.

(60) Provisional application No. 60/833,479, filed on Jul. 27, 2006.

(51) Int. Cl.
*A61K 38/00* (2006.01)
*C07K 14/22* (2006.01)
*C12P 21/02* (2006.01)

(52) U.S. Cl.
CPC ........ *C07K 14/22* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 4,414,329 A * | 11/1983 | Wegner | 435/71.1 |
| 5,672,502 A | 9/1997 | Birch et al. | |
| 6,130,062 A | 10/2000 | Milland et al. | |
| 6,413,746 B1 | 7/2002 | Field | |
| 6,660,501 B2 | 12/2003 | Field | |
| 6,692,961 B1 | 2/2004 | Judd et al. | |
| 6,998,258 B1 | 2/2006 | Kesseler et al. | |
| 7,250,274 B2 | 7/2007 | Chan et al. | |
| 7,393,676 B2 | 7/2008 | Gokarn et al. | |
| 2004/0115790 A1 | 6/2004 | Pakula et al. | |
| 2008/0026425 A1 | 1/2008 | Sun et al. | |
| 2009/0298135 A1 | 12/2009 | Maier et al. | |

FOREIGN PATENT DOCUMENTS

| | | |
|---|---|---|
| CN | 1544629 A | 11/2004 |
| RU | 2111246 C1 | 5/1998 |
| WO | 98/10088 A1 | 3/1998 |
| WO | 01/32890 A1 | 5/2001 |
| WO | 03/063766 A2 | 8/2003 |
| WO | 2004/094596 A2 | 11/2004 |
| WO | 2005/089182 A2 | 9/2005 |

OTHER PUBLICATIONS

Horn et al. (Appl. Microbiol., vol. 46, 1996, pp. 524-532).*
Amann et al, "Tightly regulated tac promoter vectors useful for the expression of unfused and fused proteins in *Escherichia coli*", Gene 69:301-315 (1988).
Ausubel et al, Current Protocols in Molecular Biology, Sections 2.10 and 6.3-6.4 (1995).
Bahat-Samet et al, "Arabinose content of extracellular polysaccharide plays a role in cell aggregation of Azospirillum brasilense", FEMS Microbiology Letters 237:195-203 (2004).
Basar et al, "Enhanced Production of Thermophilic Xylanase by Recombinant *Escherichia coli* DH5α through Optimization of Medium and Dissolved Oxygen Level", International Journal of Agriculture & Biology 12(3):321-328 (2010).
Cereghino et al, "Heterologous protein expression in the methylotrophic yeast Pichia pastoris", FEMS Microbiology Reviews 24:45-66 (2000).
Chae et al, "Framework for Online Optimization of Recombinant Protein Expression in High-Cell-Density *Escherichia coli* Cultures Using GFP-Fusion Monitoring", Biotechnology and Bioengineering 69(3):275-285 (2000).
Cserjan-Puschmann et al, "Optimizing Recombinant Microbial Fermentation Processes", Biopharm 15(7):26-34 (2002).
d'Anjou et al, "Mixed-feed exponential feeding for fed-batch culture of recombinant methylotrophic yeast", Biotechnology Letters 22:341-346 (2000).
Dinkla et al, "Effects of Iron Limitation on the Degradation of Toluene by Pseudomonas Strains Carrying the TOL (pWWO) Plasmid", Applied and Environmental Microbiology 67(8):3406-3412 (2001).
Duan et al, "Production of GST-SOD fusion protein by recombinant *E coli* XL1 Blue", Journal of Chemical Technology and Biotechnology 75:722-728 (2000).
Fletcher et al, "Vaccine Potential of the Neisseria meningitidis 2086 Lipoprotein", Infection and Immunity 72 (4):2088-2100 (2004).
Gossen et al, "Tight control of gene expression in mammalian cells by tetracycline-responsive promoters", Proc. Natl. Acad. Sci. USA 89:5547-5551 (1992).
Gossen et al, "Transcriptional Activation by Tetracyclines in Mammalian Cells", Science 268:1766-1769 (1995).
Guzman et al, "Tight Regulation, Modulation, and High-Level Expression by Vectors Containing the Arabinose PBAD Promoter" Journal of Bacteriology 177(14):4121-4130 (1995).

(Continued)

*Primary Examiner* — Hope Robinson
(74) *Attorney, Agent, or Firm* — Anna C. Chau

(57) ABSTRACT

Methods for producing proteins, for example, recombinant meningococcal 2086 proteins, using fed-batch fermentation with continuous input of an inducer after achieving a threshold parameter, and optionally continuous input of a carbon source, for example, a constant rate input, to improve protein yields, as well as high density protein compositions and compositions for use in the methods of the present invention, are provided.

33 Claims, 15 Drawing Sheets

(56) References Cited

OTHER PUBLICATIONS

Figure 1:
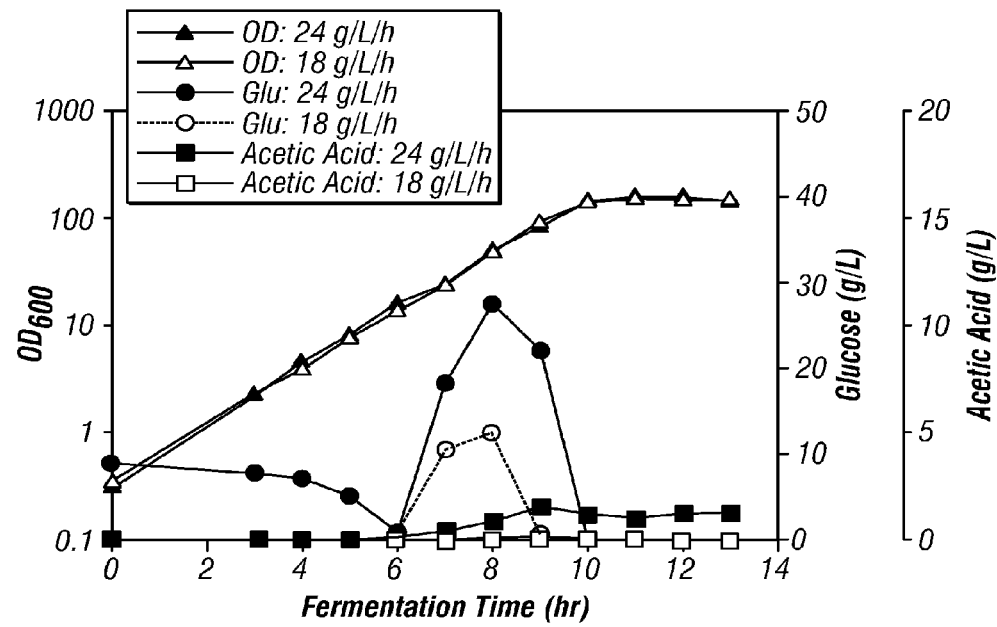

Han et al, "Characterization of an Oxygen-Dependent Inducible Promoter, the nar Promoter of *Escherichia coli*, to Utilize in Metabolic Engineering", Biotechnology and Bioengineering 72(5):573-576 (2001).

Harvey et al, "Inducible control of gene expression: prospects for gene therapy", Current Opinion in Chemical Biology 2:512-518 (1998).

Hoffman et al, "Lactose Fed-Batch Overexpression of Recombinant Metalloproteins in *Escherichia coli* BL21(DE3): Process Control Yielding High Levels of Metal-Incorporated, Soluble Protein", Protein Expression and Purification 6 (5):646-654 (1995).

Kompala et al, "Investigation of Bacterial Growth on Mixed Substrates: Experimental Evaluation of Cybernetic Models", Biotechnology and Bioengineering 28:1044-1055 (1986).

Lee et al, "Optimal Feb-Batch Control of Induced Foreign Protein Production by Recombinant Bacteria", AIChE Journal 40(5):899-907 (1994).

Magari et al, "Pharmacologic Control of a Humanized Gene Therapy System Implanted into Nude Mice", J. Clin. Invest. 100(11):2865-2872 (1997).

Mahadevan et al, "On-Line Optimization of Recombinant Product in a Fed-Batch Bioreactor", Biotechnology Progress 19(2):639-646 (2003).

No et al, "Ecdysone-inducible gene expression in mammalian cells and transgenic mice", Proc. Natl. Acad. Sci. USA 93:3346-3351 (1996).

PCT International Search Report and Written Opinion for PCT/US07/16917 issued Aug. 22, 2008.

Richieri et al, "Cell cycle dependency of monoclonal antibody production in asynchronous serum-free hybridoma cultures", Cytotechnology 5(3):243-254 (1991).

Sambrook et al, "Analysis and Cloning of Eukaryotic Genomic DNA", Molecular Cloning: A Laboratory Manual, Second Edition, Cold Spring Harbor Laboratory Press, Cold Spring Harbor, New York, Chapter 9, pp. 9.1-9.62 (1989).

Sambrook et al, "Synthetic Oligonucleotide Probes", Molecular Cloning: A Laboratory Manual, Second Edition, Cold Spring Harbor Laboratory Press, Cold Spring Harbor, New York, Chapter 11, pp. 11.1-11.61 (1989).

Sá-Nogueira et al, "The *Bacillus subtilis* L-arabinose (ara) operon: nucleotide sequence, genetic organization and expression", Microbiology 143:957-969 (1997).

Striedner et al, "Metabolic Approach for Optimization of Recombinant Fermentation Process", Recombinant Protein Production with Prokaryotic and Eukaryotic Cells, O.W. Merten et al (eds.), Kluwer Academic Publishers, pp. 179-188 (2001).

Striedner et al, "Tuning the Transcription Rate of Recombinant Protein in Strong *Escherichia coli* Expression Systems through Repressor Titration", Biotechnology Progress 19:1427-1432 (2003).

Studier et al, "Use of T7 RNA Polymerase to Direct Expression of Cloned Genes", Methods in Enzymology 185:60-89 (1990).

Sun et al, "Fermentation and Recovery Process Development for Producing Recombinant Vaccine PSPA Against *Pneumococci*" Abstract #269, Book of Abstracts (Mar. 26-30, 2000).

Thompson et al, "Control of Ammonium Concentration in *Escherichia coli* Fermentations", Biotechnology and Bioengineering 27:818-824 (1985).

Viitanen et al, "Cheese whey-induced high-cell-density production of recombinant proteins in *Escherichia coli*", Microbial Cell Factories 2:2 (2003).

Wang et al, "Positive and negative regulation of gene expression in eukaryotic cells with an inducible transcriptional regulator", Gene Therapy 4:432-441 (1997).

Wang et al, "Ligand-inducible and liver-specific target gene expression in transgenic mice", Nature Biotechnology 15:239-243 (1997).

Yee et al, "Recombinant Protein Expression in High Cell Density Fed-Batch Cultures of *Escherichia Coli*", Biotechnology 10:1150-1556 (1992).

Zhou et al, "Feb-Batch Culture of Recombinant NS0 Myeloma Cells with High Monoclonal Antibody Production", Biotechnology and Bioengineering 55(5):783-792 (1997).

* cited by examiner

Lane 1. MWt Standard; Lane 2. rLP2086; Lane 3. Pre-induction; Lane 4. Induction 1.1 hr;
Lane 5. Induction 2.0 hr; Lane 6. Induction 3.0 hr; Lane 7. Induction 3.6 hr; Lane 8. Induction 4.0 hr Lane 1. MWt Standard; Lane 2. rLP2086 (A); Lane 3. Pre-induction; Lane 4. Induction 1.1 hr; Lane 5. Induction 2.0 hr; Lane 6. Induction 3.1 hr; Lane 7. Induction 3.6 hr; Lane 8. Induction 4.0 hr

HIGH-CELL DENSITY FED-BATCH FERMENTATION PROCESS FOR PRODUCING RECOMBINANT PROTEIN

RELATED APPLICATIONS

This application is a continuation of U.S. patent application Ser. No. 11/829,703, filed on Jul. 27, 2007, now U.S. Pat. No. 8,632,995, which claims priority to U.S. Provisional Patent Application Ser. No. 60/833,479, entitled HIGH-CELL DENSITY FED-BATCH FERMENTATION PROCESS FOR PRODUCING RECOMBINANT PROTEIN, filed on Jul. 27, 2006, the disclosure of which is herein incorporated by reference in its entirety.

FIELD OF THE INVENTION

This application relates generally to novel fed-batch fermentation methods that provide improved protein expression in bacterial systems, as well as high density protein compositions and compositions that are used in the novel fed-batch fermentation methods.

BACKGROUND OF THE INVENTION

Various fermentation strategies have been used to produce proteins in sufficient quantities for laboratory, clinical or commercial use. Fed-batch fermentation has been used to provide increased proteins yields over those provided by simple batch fermentation methods. Fed-batch fermentation is a process in which, after an initial batch phase, a phase takes place in which one or more nutrients are supplied to the culture by feeding.

Generally, during the batch phase, cells are initially grown to a desired concentration. At this phase, cell growth is amplified and generally no target protein will be produced unless one adds an inducer, such as arabinose, lactose or isopropyl beta-D-thiogalactoside (IPTG), depending on the promoter, or there is some leakage of the promoter. During the feed phase, carbon source and other requirements are typically fed to a fermentor in a relatively concentrated liquid stream at a certain feed rate. Once a target cell density is achieved, a feed is commenced with the inducer or the inducer and other nutrients. In this phase, the emphasis is on protein production by the grown cells. Substrate (that is, the nutrients and the inducer) that is fed to the fermentor is at this stage used generally for cell growth and product synthesis. The cell growth is controlled by the feed rate to obtain an optimum cell growth and production of protein. During the protein production stage, an inducer must be added for recombinant organisms.

Protein expression on a medium comprising a common carbon source such as glucose or another sugar based carbon source and an inducer is satisfactory until limiting conditions arise at the end of the feed phase. Examples of limiting conditions include reduced oxygen concentration, reduced nutrients such as vitamins, carbon, nitrogen and accumulation of toxic compounds in the growth medium.

Fed-batch fermentation strategies often involve different forms of feedback control, including indirect and direct feedback to control the supply of nutrients. One such fed-batch fermentation method involves application of a feedback control algorithm by feeding nutrients in order to control a process parameter at a defined set point. For example, direct control of feed may be based on measurement of nutrient concentration. Feedback control is then directly related to cell activity throughout fermentation. Control parameters which have been used for feedback control of fermentations include pH value, on line measured cell density or dissolved oxygen tension (DOT).

However, the application of feedback algorithms is accompanied by a number of disadvantages. One such disadvantage is that the feed rate depends on current process parameters. Any disturbance to the process may affect the parameter thus distorting the feed rate and resulting protein yield. Such disadvantages are magnified as the process is scaled-up to produce increased protein quantities.

Another disadvantage of previously employed fed-batch strategies is that when using feed-back control, the specific growth rate cannot be exactly predefined or controlled, resulting in suboptimal yields in processes, where the product formation is dependent on growth.

Further, when carbon flux (for example, high glucose concentration) into the central metabolic pathway exceeds the maximum capacity of the Tricarboxylic Acid (TCA) cycle, by-products may accumulate. The accumulation of by-products could inhibit cell growth and protein production during fermentation.

Additionally, the various deficiencies of fed-batch fermentation methods often result in inefficient use of nutrient components. As such, the methods may be economically disadvantageous, particularly for large scale commercial protein production.

Previous approaches to recombinant protein expression through fed-batch fermentation, as described above, have various deficiencies. Given the importance of cost-effectively producing sufficient quantities of protein for various purposes, there is a need for an efficient fed-batch fermentation method that results in higher cell growth, increased product formation (that is, higher protein yield), and decreased by-product accumulation.

SUMMARY OF THE INVENTION

The present invention relates to novel fed-batch fermentation methods for producing unexpectedly high yields of recombinant protein.

An embodiment of the present invention provides a method for producing a recombinant protein comprising: culturing a recombinant bacterial cell to express a recombinant protein comprising continuously adding a carbon source to a culture comprising the recombinant bacterial cell and continuously adding an inducer to the culture after the culture achieves a threshold parameter; and isolating the recombinant protein from the cell culture.

A further embodiment of the present invention provides a method for producing a recombinant protein comprising: (a) introducing into a bacterial host cell an expression vector encoding a recombinant protein under the control of an inducible promoter to form a recombinant bacterial cell; (b) introducing the recombinant bacterial cell into a culture medium to form a cell culture; (c) adding a carbon source to the cell culture as a continuous feed; (d) monitoring cell growth in the cell culture for achievement of a threshold optical density ($OD_{600}$); (e) adding an inducer of the inducible promoter to the cell culture as a continuous feed once the threshold optical density ($OD_{600}$) is achieved; and (f) harvesting the recombinant protein from the cell culture.

A still further embodiment of the present invention provides a method for producing a recombinant protein comprising: culturing a recombinant bacterial cell to express a recombinant protein by continuously adding an inducer to a culture comprising the bacterial cell after the culture achieves a threshold parameter, wherein the bacterial cell comprises a nucleic acid sequence corresponding to a gene of *N. meningitidis* serogroup B.

According to an even further embodiment, the present invention provides a method for producing a recombinant 2086 protein (rP2086) comprising: (a) introducing into a bacterial host cell an expression vector encoding a recombinant meningococcal 2086 protein under the control of an inducible promoter to form a recombinant bacterial cell; (b) introducing the recombinant bacterial cell to a culture medium to form a culture; (c) adding a carbon source to the culture; (d) monitoring cell growth in the culture for achievement of a threshold optical density (OD); (e) continuously adding an inducer of the inducible promoter to the culture once the cell density of the culture achieves an optical density of about 70 to 110; and (f) harvesting the recombinant meningococcal 2086 protein from the culture after about 3 hours to about 6 hours after commencement of continuously adding the inducer.

According to another embodiment, the present invention provides a composition comprising: a bacterial culture comprising a recombinant 2086 protein (rP2086) at a density of at least about 1.5 g/L based on the total volume of the bacterial culture.

According to yet another embodiment, the present invention provides a composition comprising: a bacterial culture medium comprising a recombinant meningococcal 2086 protein (rP2086) prepared according to the methods of the present invention.

BRIEF DESCRIPTION OF THE DRAWINGS

FIG. 1: Fed-batch fermentation at various constant feed rates without induction.

FIG. 2: Fed-batch fermentation at various constant feed rates without induction.

FIG. 3: Induction at various optical densities.

FIG. 4: Induction with various arabinose levels.

FIG. 5: Effects of arabinose addition method on rLP2086 yield.

FIG. 6: Effect of arabinose feed rate on rLP2086 production.

FIG. 7: Effect of induction time on expression.

FIG. 8: Fed-batch fermentation for subfamily B rLP2086 production.

FIGS. 9*a* and 9*b*: SDS-PAGE and Western Blot of rLP2086 subfamily B induction, respectively.

FIG. 10: Fed-batch fermentation for subfamily A rLP2086 production.

FIGS. 11*a* and 11*b*: SDS-PAGE and Western Blot of rLP2086 subfamily A induction, respectively.

FIGS. 12*a*, 12*b* and 12*c*: Dual feed of glucose and arabinose during induction.

FIG. 13*a*: rLP2086 subfamily B *E. coli* fed-batch fermentation at 100 L scale.

FIG. 13*b*: rLP2086 subfamily A *E. coli* fed-batch fermentation at 100 L scale.

FIG. 14*a*: rIP2086 subfamily B *E. coli* fed-batch fermentation with dual glucose and arabinose feed at 100 L scale.

FIG. 14*b*: rIP2086 subfamily A *E. coli* fed-batch fermentation with dual glucose and arabinose feed at 100 L scale.

DETAILED DESCRIPTION OF THE INVENTION

The methods of the present invention are based on the surprising discovery that unexpectedly high protein yields are obtained by fed-batch fermentation with continuous feeding of an inducer during induction in a culture medium. Optionally, a carbon source is continuously fed prior to and/or during the continuous inducer feed. When induced by arabinose, about 2-3 g/L of a recombinant 2086 lipoprotein (rLP2086) (which is expressed by a microorganism having a sequence corresponding to the 2086 gene in *N. meningitidis* serogroup B) was produced in accordance with an embodiment of the invention. This represents approximately a 2-3-fold increase in rLP2086 yield by fed-batch fermentation for both subfamilies A and B of the 2086 protein compared to a comparative batch fermentation process. Moreover, the methods of the present invention are readily adaptable to commercial scale production of these and other proteins.

For the purposes of promoting an understanding of the embodiments described herein, reference will be made to various embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Likewise, the singular forms of terms such as "medium" include reference to the plural "media", and vice versa. Thus, for example, a reference to "a culture medium" includes a plurality of such media, as well as a single medium; and a reference to "culture medium" includes a plurality of media, as well as a single medium.

The term "inducer", as used herein, refers to any agent that induces, enhances, or promotes expression of a recombinant protein, whereby gene expression under the control of the inducible promoter can be directly regulated by the concentration of that agent.

The term "carbon source", as used herein, refers to a source of carbon and energy for cells.

The terms "feed", "fed", "feeding" or "continuously adding", as used interchangeably herein, refer to adding a substance continuously over a period of time rather than all at once. The terms contemplate a single initiation and/or termination or multiple start and/or stop points for continuously adding the substance during a fermentation process.

The term "recombinant protein", as used herein, refers to any protein or biologically active portion thereof (for example, a portion that retains biological activity of the full protein) that is not a reporter or marker gene (for example, a green fluorescent protein) expressed from recombinant genetic material encoding amino acids, including peptides, polypeptides, proteins, oligoproteins and/or fusion proteins. A recombinant protein product may include a therapeutic, prophylactic or diagnostic product.

Methods of the Present Invention

The methods of the present invention provide unexpectedly high yields of protein through a novel fed-batch fermentation process involving continuously adding an inducer, such as arabinose, to a culture medium after the culture achieves a threshold parameter. A carbon source, such as glucose, is generally added to a culture comprising a recombinant bacterial cell prior to the induction phase. The carbon source may be fed together with the inducer. The inducer may also serve as a secondary carbon source.

A carbon source, such as glucose, is continuously added to the culture medium, before and/or during the continuous feed of the inducer to the culture medium, in accordance with an embodiment of the present invention. Thus, the continuous feed of the carbon source overlaps the continuous feed of the inducer, according to an embodiment. The continuous feed of the carbon source may continue during the entire duration of the continuous inducer feed or only during part(s) of that duration. In another embodiment, the continuous feed of the carbon source does not overlap the continuous feed of the inducer. According to an embodiment of the present invention, the inducer and/or carbon source may be fed to the culture at a constant rate.

The fed-batch fermentation process involves several steps resulting in the production of the desired protein in accordance with an embodiment of the invention. In an initial step, an expression vector that encodes a recombinant protein product under the control of an inducible promoter is prepared and then is introduced into a bacterial host cell. The bacterial host cell is introduced into a culture medium. An inducer of the inducible promoter is fed to the culture (that is, the inducer is added into the culture continuously over a period of time). The inducer may be fed to the culture at a constant rate. Then, the recombinant protein product is harvested from the culture. The recombinant protein produced in this manner may then be purified as desired and/or used in any suitable manner, such as in a prophylactic, therapeutic or diagnostic formulation.

High cell density and enhanced protein yield was unexpectedly achieved by fed-batch fermentation with the constant rate feeding of an inducer, which provides a yield of recombinant protein product of approximately a 2-3-fold increase as compared to batch fermentation, as illustrated in the examples provided below. The methods of the present invention are applicable to large-scale fermentation as well as small-scale fermentation. "Large-scale" fermentation, as used herein, refers to fermentation in a fermentor that is at least approximately 1,000 L in volumetric capacity, that is, working volume, leaving adequate room for headspace. "Small-scale" fermentation refers generally to fermentation in a fermentor that is generally no more than approximately 100 L in volumetric capacity, such as 5 L, 10 L, 50 L or 100 L. A demonstrated advantage of the present fed-batch fermentation process is that it may be utilized for the production of a recombinant protein product at the 5-10 L fermentor scale and is scalable to any volume, for example, 100 L, 150 L, 250 L, 500 L, 1000 L or more, without limitation.

Inducers:

The methods described herein relate to the production of recombinant protein wherein the expression of recombinant protein is under the transcriptional control of an inducible promoter, whereby gene expression under the control of the inducible promoter can be directly regulated by the concentration of the inducer present in the culture medium. The inducer is continuously provided to a culture medium, optionally at a constant rate. The inducer is added to the culture medium once a threshold parameter has been achieved. For example, a recombinant protein may be under the control of the araB promoter (for example, ParaB) that can be directly regulated by the concentration of arabinose that is added at a constant rate to the culture medium. Suitable inducers for use in conjunction with the present invention are well known to persons skilled in the art. Examples of inducers of the present invention are provided below, without limitation.

| Promoter | Inducer |
|---|---|
| Arabinose promoter, such as, ParaB | Arabinose |
| human Plasminogen | Tumor Necrosis Factor, |
| Activator Inhibitor type-1, Hpai-1 | TNF |
| Cytochrome P-450 | Toxins |
| CYP1A1 Metal-Responsive Element, | Heavy Metals, Mouse |

-continued

| Promoter | Inducer |
|---|---|
| MRE | Mammary |
| Tumor Virus | Glucocorticoids |
| Collagenase | Phorbol Ester |
| Stromolysin | Phorbol Ester |
| SV40 | Phorbol Ester |
| Proliferin | Phorbol Ester |
| α-2-Macroglobulin | IL-6 |
| Murine MX Gene | Interferon, Newcastle Disease Virus |
| Vimectin | Serum |
| Thyroid Stimulating Hormone α. Gene Antigen Tumor Necrosis Factor | Thyroid Hormone HSP70 Ela, SV40 Large T FMA |
| Interferon | Viral Infection, dsRNA |
| Somatostatin | Cyclic AMP |
| Fibronectin | Cyclic AMP |
| lac promoter/operator | IPTG |

Carbon Source

Any suitable carbon source, for example, glycerol, succinate, lactate, or sugar-based carbon source, for example, glucose, lactose, sucrose, and fructose, is contemplated for use in the present invention, as would be understood by a person of ordinary skill in the art. For example, sugar-based carbon sources that may be used in the present invention include, without limitation, branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (for example, polymannuronic acid, or alginic acid), D-glucosamine, D-galactosamine, D-glucose and neuraminic acid including homopolysaccharides and heteropolysaccharides for example, lactose, amylopectin, starch, hydroxyethyl starch, amylose, dextran sulfate, dextran, dextrins, glycogen, or the polysaccharide subunit of acid mucopolysaccharides, for example, hyaluronic acid; polymers of sugar alcohols such as polysorbitol and polymannitol; heparin or heparan; or any combination thereof, without limitation. Glucose is the primary carbon source according to an embodiment of the invention. Arabinose, when used as the inducer, may also serve as a secondary carbon source, although it may be the primary carbon source as well. According to an embodiment, the carbon sources include any of D-glucose, L-arabinose, sucrose, I-inositol, D-mannitol, β-D-fructose, α-L rhammnose, D-xylose, cellulose, or any combination thereof. One or more than one carbon source may be used in the present invention.

Bacterial Expression Systems and Plasmids

This invention also provides recombinant bacterial cells comprising an expression vector, such as a plasmid, comprising an expression control sequence having promoter sequences and initiator sequences and a nucleotide sequence which codes for a desired polypeptide, the nucleotide sequence being located 3' to the promoter and initiator sequences. Any suitable expression control sequence and host cell/cloning vehicle is contemplated, as would be known to a person of skill in the art based upon the disclosure provided herein.

Suitable expression control sequences and host cell/cloning vehicle combinations are well known in the art, and are described by way of example, in Sambrook, J., E. F. Fritsch, and T. Maniatis, 1989, *Molecular Cloning: A Laboratory Manual*, Cold Spring Harbor Laboratory Press, Cold Spring Harbor, N.Y. In general, recombinant DNA techniques involve obtaining by synthesis or isolation a DNA sequence that encodes the recombinant protein of interest, and introducing it into an appropriate vector/host cell expression system where it is expressed, preferably under the control of an arabinose inducible promoter. Any of the methods described for the insertion of DNA into an expression vector may be used to ligate a promoter and other regulatory control elements into specific sites within the selected recombinant vector. Suitable host cells are then transformed, infected, transduced or transfected with such vectors or plasmids by conventional techniques.

A variety of host cell-vector (plasmid) systems may be used to express the recombinant protein of interest. The vector system, such as for example a system including the arabinose inducible promoter, is compatible with the host cell used. The DNA encoding the recombinant protein product of interest is inserted into an expression system, and the promoter (preferably the arabinose inducible promoter), and other control elements are ligated into specific sites within the vector so that when the vector is inserted into a host cell (by transformation, transduction or transfection, depending on the host cell-vector system used) the DNA encoding the recombinant protein product of interest is expressed by the host cell.

The vector may be selected from one of the viral vectors or non-viral vectors described above but must be compatible with the host cell used. The recombinant DNA vector may be introduced into appropriate host cells (bacteria, virus, yeast, mammalian cells or the like) by transformation, transduction or transfection, etc. (depending upon the vector/host cell system). Host-vector systems include but are not limited to bacteria transformed with bacteriophage DNA, plasmid DNA or cosmid DNA.

The expression in prokaryotes of the recombinant protein product of interest may be carried out in any suitable species or strain of bacteria, such as E. coli, with vectors containing constitutive or inducible promoters directing the expression of either fusion or non-fusion proteins.

Fusion vectors add a number of amino acids to a protein encoded therein, to the amino or carboxy terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include Pgex (Pharmacia Biotech Inc; Smith and Johnson, 1988), Pmal (New England Biolabs, Beverly; Mass.) and Prit5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al. (1988) Tightly regulated tac promoter vectors useful for the expression of unfused and fused proteins in Escherichia coli, Gene, 69, 301-315), and Pet lid (Studier et al. (1990) Use of T7 RNA polymerase to direct expression of cloned genes, Methods in Enzymology, 185, 60-89). Target gene expression from the pTrc vector relies on host RNA polymerase transcription from a hybrid trp-lac fusion promoter. Target gene expression from the Pet lid vector relies on transcription from a T7 gn1 0-lac fusion promoter mediated by a coexpressed viral RNA polymerase J7 gnl. This viral polymerase is supplied by host strains BL21 (DE3) or HMS I 74(DE3) from a resident prophage harboring a T7 gnl gene under the transcriptional control of the IacUV 5 promoter.

The regulatory sequence of the vector construct is an inducible promoter according to an embodiment. The use of an inducible promoter will permit low basal levels of activated protein to be produced by the cell during routine culturing and expansion add. Subsequently, the cells may then be induced to express large amounts of the desired protein during production or screening. The inducible promoter may be isolated from cellular or viral genomes.

Inducible promoters that are regulated by exogenously supplied compounds, include, without limitation, the arabinose promoter, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., 1996 Proc. Natl. Acad. Sci. USA, 93:3346-3351), the tetracycline-repressible system (Gossen et al., 1992 Proc. Natl. Acad. Sci. USA, 89:5547-5551), the tetracycline-inducible system (Gossen et al., 1995 Science, 268:1766-1769, see also Harvey et al., 1998 Curr. Opin. Chem. Biol, 2:512-518), the RU486-inducible system (Wang et al., 1997 Nat. Biotech., 15:239-243 and Wang et al., 1997 Gene Ther., 4:432-441) and the rapamycin-inducible system (Magari et al., 1997 J. Clin. Invest., 100: 2865-2872). According to an embodiment of the invention, the promoter is an arabinose inducible promoter.

Any suitable bacterial host cell is contemplated for use in the present invention as would be understood by a person skilled in the art based upon the disclosure provided herein. For example, suitable bacteria for this purpose include Escherichia, Enterobacter, Azotobacter, Erwinia, Bacillus, Pseudomonas, Klebsiella, Proteus, Salmonella, Serratia, Shigella, Rhizobia, Vitreoscilla, Paracoccus, or a combination thereof, without limitation. Any suitable strain of any such suitable bacteria is also contemplated by the present invention. Further, the use of suitable mutated cells, as would be recognized by a person of skill in the art, is also contemplated by the present invention. A person of skill in the art would readily be able to select an appropriate host cell to use under specific circumstances based upon the guidance provided herein.

Examples of suitable inducible E. coli expression vectors include, without limitation, pTrc (Amann et al., 1988 Gene, 69:301-315), the arabinose expression vectors (for example, Pbad18, Guzman et al., 1995 J. Bacteriol., 177:4121-4130), and pETlld (Studier et al., 1990 Methods in Enzymology, 185:60-89). Target gene expression from the pTrc vector relies on host RNA polymerase transcription from a hybrid trp-lac fusion promoter. Target gene expression from the pETlld vector relies on transcription from a T7 gn10-lac fusion promoter mediated by a coexpressed viral RNA polymerase T7 gn 1. This viral polymerase is supplied by host strains BL21 (DE3) or HMS 174(DE3) from a resident prophage harboring a T7 gn1 gene under the transcriptional control of the lacUV5 promoter. The $P_{BAD}$ system relies on the inducible arabinose promoter that is regulated by the araC gene. The promoter is induced in the presence of arabinose.

Other embodiments of the present invention utilize arabinose-regulated expression vectors, or vectors where the expression of the recombinant protein of interest is under the control of an arabinose promoter, for example, the promoter for the E. coli arabinose operon, $P_{BAD}$ or $P_{ARA}$, without limitation.

A nucleic acid (nucleotide) sequence encoding any desired protein is contemplated by the present invention. The nucleotide sequence may be a full or partial naturally-occurring nucleotide sequence or a full or partial altered nucleotide sequence, or any sequence that hybridizes thereto under stringent conditions. References herein to nucleic acid sequences that correspond to a gene refer to any nucleic acid sequence expressible as the desired protein.

For example, such altered nucleic acid sequences include one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in any sequence by the numerical percent of the respective percent identity (divided by 100) and subtracting that product from said total number of nucleotides in said sequence.

For instance, the present invention contemplates use of a nucleotide sequence that has at least 70% identity to a certain nucleic acid sequence; a degenerate variant thereof or a fragment thereof, wherein the sequence may include up to $n_n$ nucleic acid alterations over the entire polynucleotide region of the nucleic acid sequence, wherein $n_n$ is the maximum number of alterations and is calculated by the formula:

$$n_n = x_n - (x_n \cdot y),$$

in which $x_n$ is the total number of nucleic acids of any sequence and y has a value of 0.70, wherein any non-integer product of $x_n$ and y is rounded down to the nearest integer prior to subtracting such product from $x_n$. Of course, y may also have a value of 0.80 for 80%, 0.85 for 85%, 0.90 for 90%, 0.94 for 94%, 0.95 for 95%, 0.96 for 96%, 0.97 for 97%, 0.98 for 98%, or 0.99 for 99%, etc. Alterations of a sequence may create nonsense, missense or frameshift mutations in this coding sequence and thereby alter the polypeptide encoded by the polynucleotide following such alterations.

The present invention contemplates the use of degenerate variants, or a fragment thereof. As defined herein, a "degenerate variant" is a polynucleotide that differs from the nucleotide sequence (and fragments thereof) due to degeneracy of the genetic code, but still encodes the same protein The nucleic acid may comprise DNA, chromosomal DNA, cDNA and RNA and may further comprise heterologous nucleotides. In accordance with various embodiments, the nucleic acid hybridizes to a certain nucleic acid, a complement thereof, a degenerate variant thereof, or a fragment thereof, under high stringency hybridization conditions. In yet other embodiments, the polynucleotide hybridizes under intermediate stringency hybridization conditions.

It will be appreciated that the nucleic acids may be obtained from natural, synthetic or semi-synthetic sources; furthermore, the nucleotide sequence may be a naturally occurring sequence, or it may be related by mutation, including single or multiple base substitutions, deletions, insertions and inversions, to such a naturally occurring sequence. The nucleic acid molecule may be RNA, DNA, single stranded or double stranded, linear or covalently closed circular form.

Examples Of stringency conditions are shown in the Stringency Conditions Table below: highly stringent conditions are those that are at least as stringent as, for example, conditions A-F; stringent conditions are at least as stringent as, for example, conditions G-L; and reduced stringency conditions are at least as stringent as, for example, conditions M-R.

Stringency Conditions

| Stringency Condition | Polynucleotide Hybrid | Hybrid Length (bp)[I] | Hybridization Temperature and Buffer[H] | Wash Temperature and Buffer[H] |
|---|---|---|---|---|
| A | DNA:DNA | >50 | 65EC; 1xSSC -or- 42EC; 1xSSC, 50% formamide | 65EC; 0.3xSSC |
| B | DNA:DNA | <50 | $T_B$; 1xSSC | $T_B$; 1xSSC |
| C | DNA:RNA | >50 | 67EC; 1xSSC -or- 45EC; 1xSSC, 50% formamide | 67EC; 0.3xSSC |
| D | DNA:RNA | <50 | $T_D$; 1xSSC | $T_D$; 1xSSC |
| E | RNA:RNA | >50 | 70EC; 1xSSC -or- 50EC; 1xSSC, 50% formamide | 70EC; 0.3xSSC |
| F | RNA:RNA | <50 | $T_F$; 1xSSC | $T_F$; 1xSSC |
| G | DNA:DNA | >50 | 65EC; 4xSSC -or- 42EC; 4xSSC, 50% formamide | 65EC; 1xSSC |
| H | DNA:DNA | <50 | $T_H$; 4xSSC | $T_H$; 4xSSC |
| I | DNA:RNA | >50 | 67EC; 4xSSC -or- 45EC; 4xSSC, 50% formamide | 67EC; 1xSSC |
| J | DNA:RNA | <50 | $T_J$; 4xSSC | $T_J$; 4xSSC |
| K | RNA:RNA | >50 | 70EC; 4xSSC -or- 50EC; 4xSSC, 50% formamide | 67EC; 1xSSC |
| L | RNA:RNA | <50 | $T_L$; 2xSSC | $T_L$; 2xSSC |
| M | DNA:DNA | >50 | 50EC; 4xSSC -or- 40EC; 6xSSC, 50% formamide | 50EC; 2xSSC |
| N | DNA:DNA | <50 | $T_N$; 6xSSC | $T_N$; 6xSSC |
| O | DNA:RNA | >50 | 55EC; 4xSSC -or- 42EC; 6xSSC, 50% formamide | 55EC; 2xSSC |
| P | DNA:RNA | <50 | $T_P$; 6xSSC | $T_P$; 6xSSC |
| Q | RNA:RNA | >50 | 60EC; 4xSSC -or- 45EC; 6xSSC, 50% formamide | 60EC; 2xSSC |
| R | RNA:RNA | <50 | $T_R$; 4xSSC | $T_R$; 4xSSC | bp[I]: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarities.

buffer[H]: SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.

$T_B$ through $T_R$: The hybridization temperature for hybrids anticipated to be less than 50 base pairs in length should be 5-10EC less than the melting temperature ($T_m$) of the hybrid, where $T_m$ is determined according to the following equations. For hybrids less than 18 base pairs in length, $T_m(EC)=2(\#$ of A+T bases)$+4(\#$ of G+C bases). For hybrids between 18 and 49 base pairs in length, $T_m(EC)=81.5+16.6(\log_{10}[Na^+]+ 0.41(\% G+C)-(600/N)$, where N is the number of bases in the hybrid, and $[Na^+]$ is the concentration of sodium ions in the hybridization buffer ($[Na^+]$ for 1xSSC=0.165 M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and Current *Protocols in Molecular Biology*, 1995, F. M. Ausubel et al., eds., John Wiley & Sons, Inc., sections 2.10 and 6.3-6.4, incorporated herein by reference.

The invention contemplates using polynucleotides that are fully complementary to these polynucleotides as well as antisense sequences. The antisense sequences, also referred to as antisense oligonucleotides, include both internally generated and externally administered sequences that block expression of polynucleotides encoding the polypeptides of the invention. The antisense sequences of the invention comprise, for example, about 15-20 base pairs, without limitation. The antisense sequences can be designed, for example, to inhibit transcription by preventing promoter binding to an upstream nontranslated sequence or by preventing translation of a transcript encoding a polypeptide of the invention by preventing the ribosome from binding.

The polynucleotides may be prepared or obtained in any suitable manner (for example, by chemical synthesis, from DNA libraries, from the organism itself) and can take various forms (such as, single-stranded, double-stranded, vectors, probes, primers) as would be understood by persons of skill in the art. The term "polynucleotide" includes DNA and RNA, and also their analogs, such as those containing modified backbones. According to further implementations of the present invention, the polynucleotides comprise a DNA library, such as a cDNA library.

2086 Protein Expression Systems:

A recombinant microorganism capable of expressing a Neisseria meningitidis serogroup B 2086 polypeptide is provided in accordance with an embodiment of the present invention. The recombinant microorganism comprises an expression control sequence having promoter sequences and initiator sequences, and a nucleotide sequence which codes for a 2086 polypeptide, the nucleotide sequence being located 3' to the promoter and initiator sequences. In a further aspect, there is provided a host cell comprising a recombinant 2086 polynucleotide as described herein and in WO 03/063766 and WO 04/094596, which are incorporated herein by reference in their entirety. As such the present invention provides a method for producing a recombinant 2086 protein, as described in WO 03/063766 and WO 04/094596, for example, without limitation.

Once host cells expressing a desired protein or polypeptide of the invention have been constructed by transforming, transfecting or infecting host cells with plasmids containing the corresponding 2086 polynucleotide, the host cells are cultured under conditions such that the polypeptides are expressed in accordance with the methods of the present invention. The polypeptide may then be isolated substantially free of contaminating host cell components by techniques well known to those skilled in the art.

Threshold Parameters:

Several parameters may be used to monitor and control the progress of the culture in terms of cell growth and recombinant protein expression. Such parameters include, but are not limited to, optical density (OD), dissolved oxygen (DO), pH, nutrient/energy consumption (such as carbon source), accumulation of metabolic by-products (for example, acetic acid), harvest time, and temperature. Any suitable parameter or combination of parameters is contemplated for use in the present invention, as would be understood by a person of ordinary skill in the art, based upon the guidance provided herein.

A threshold parameter is established to determine the point at which the inducer is to be continuously added to the culture (that is, fed to the culture over time). The threshold parameter is a predetermined parameter. An appropriate threshold parameter, such as a predetermined optical density, is readily determined by a person of skill in the art based upon the guidance provided herein in accordance with various embodiments of the present invention. One threshold parameter or a combination of threshold parameters may be used.

The parameter or combination of parameters may be monitored at any suitable time intervals in the culture. For example, $OD_{600}$ and glucose concentrations may be monitored at one-hour, half-hour, or quarter-hour intervals, without limitation.

The optical density is used as the threshold parameter for initiation of the continuous inducer feed in accordance with an embodiment of the present invention. When the cell density of the culture achieves a predetermined threshold parameter, such as an optical density of about 70 to about 110, the inducer is then fed to the culture as described herein. A narrower range may be established for the threshold parameter. For instance, the present invention contemplates that one may initiate the continuous addition of the inducer to the culture when cell density of the culture achieves an optical density about 70 to about 105, about 75 to about 100, about 75 to about 95, about 75 to about 85, about 76 to about 84, about 78 to about 82, or about 80, in accordance with embodiments of the present invention.

The present invention also contemplates the use of threshold parameters to signal the initiation and/or termination of the feeding of the carbon source.

Any suitable device or combination of devices is contemplated for use in monitoring the threshold parameter(s), as would be known to persons of skill in the art. For instance, a probe or combination of probes for measuring a threshold parameter, may be mounted on the fermentation device (the "fermentor") in any suitable manner, without limitation.

Constant Feed Rates:

The constant feed rates refer to the rate at which the inducer(s) and/or carbon source(s) is added to the culture. The inducer is added to the culture after a threshold parameter has been achieved. The carbon source may also be added to the culture after a threshold parameter is achieved (and likewise, addition of the carbon source may be terminated upon achieving a threshold parameter). These threshold parameters include, without limitation, optical density (OD), dissolved oxygen (DO), pH, concentration of nutrient in the culture medium, total concentration of the first carbon source added to the culture medium, or any combination thereof.

Any suitable constant rate is used to continuously add the inducer and/or carbon source to the culture as would be understood by a person skilled in the art based upon the guidance provided herein. In accordance with various embodiments of the present invention, a suitable constant rate is determined by DO-stat, as described in the examples below. For example, a feed rate equivalent to the DO-stat controller may be selected by adding enough glucose to bring the concentration up to 15 and 24 g/L every hour, without limitation.

For example, the inducer and/or carbon source may be added to the culture at a constant rate until a certain amount of inducer and/or carbon source, such as from about 4 g/L to about 40 g/L, such as, 4 g/L, 5 g/L, 6 g/L, 7 g/L, 8 g/L, 9 g/L, 9.5 g/L, 9.75 g/L, 10 g/L, 10.25 g/L, 10.5 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, based on the total volume of the culture, has been added to the culture, without limitation. According to various embodiments, the total amount of inducer and/or carbon source fed to the culture is about 5 g/L to about 20 g/L, 7 g/L to about 15 g/L, 8 g/L to about 14 g/L, 9 g/L to about 11 g/L, or about 10 g/L.

The total amount of inducer to be added to the culture may be offset by the total amount of carbon source added to the culture. For instance, when the carbon source is glucose and the inducer is arabinose, the amount of inducer added may be reduced by addition of glucose. For example, in an embodiment, a total of 10 g/L of an inducer (that is, such as arabinose is added to a culture and 11 g/L of a carbon source, such as glucose is added. The protein yield obtained in this manner approximates the yield when a total amount of 20 g/L of arabinose (that is, 20,000 g or 20 kg total in a 1,000 L culture of arabinose) and no glucose is used. Thus, this offset provided by the present methods is advantageous given the high cost of arabinose relative to glucose.

According to various embodiments of the invention, the constant rate at which the inducer and/or carbon source is added to the culture may be set in the range from about 1.5 g/L to about 24 g/L every hour. For example, where the carbon source is glucose, the constant rate for the addition of glucose may include, without limitation, 1.8 g glucose/L/h, 3.3 g glucose/L/h, 6.7 g glucose/L/h, 15 g glucose/L/h, 16.4 g glucose/L/h, 18 g glucose/L/h, 24 g glucose/L/h, etc. According to various embodiments, an inducer such as arabinose is added at constant rates of about 1.5 g/L/h to about 16 g/L/h.

According to various embodiments, once a threshold parameter has been achieved, the feed on the carbon source may be continued, stopped or temporarily interrupted. The feed of the carbon source may be interrupted in which case the feed will re-start at the constant rate once a threshold for starting the feed has been achieved. Thus, according to an embodiment, a start threshold and a stop threshold may be used to regulate the feed of the carbon source into the culture. According to another embodiment, both glucose and arabinose are fed at a constant rate based on the threshold parameter, without stopping or restarting the feed.

The appropriate total amount of carbon source to add to any specific culture can be readily determined by a person of skill in the art based upon the guidance provided herein. The total amount of carbon source added to the culture may range from about 1 g/L to about 100 g/L (based on the total volume in liters of the culture) according to an embodiment of the present invention. For example, according to an embodiment, 50 g/L of glucose is added during the growth phase by starting with 10 g/L in the medium, commencing the constant rate glucose feed when the glucose level reaches zero, and continuing the constant rate glucose feed until OD achieves 80 at which time about 40 g/L of glucose will have been fed in addition to the initial 10 g/L of glucose. According to an embodiment, the total amounts of carbon source are provided in concentrated form for ease of scalability. These amounts are readily converted into the total mass of the carbon source to be used in a particular circumstance. For example, when 10 g/L of carbon source is to be added to a 1,000 L culture, the total amount of carbon source to be added is readily determined as 10 g/L×1,000 L=10,000 grams (or 10 kg) of total carbon source. The total amount of carbon source added may serve as a threshold parameter in accordance with various embodiments as described herein.

The appropriate total amount of inducer to add to any specific culture may be readily determined by a person of skill in the art based upon the guidance provided herein. The total amount of inducer added to the culture may range from about 4 g/L to about 40 g/L (based on the total volume in liters of the culture) in accordance with various embodiments. According to various embodiments, the total amount of carbon source added to the culture is about 5 g/L to about 20 g/L, 7 g/L to about 15 g/L, 8 g/L to about 14 g/L, 9 g/L to about 11 g/L, or about 10 g/L based on the total volume of the culture. According to an embodiment, the total amounts of inducer are provided in concentrated form for ease of scalability. These amounts are readily converted into the total mass of the inducer to be used in a particular circumstance. For example, when 10 g/L of inducer is to be added to a 1,000 L culture, the total amount of inducer to be added is readily determined as 10 g/L×1,000 L=10,000 grams (or 10 kg) of total inducer.

The fresh culture medium will typically contain an initial amount of a first carbon source at the time of inoculation with a host cell, thus creating a culture. This initial concentration may be monitored and the concentration of the first carbon source used as a threshold parameter.

Any suitable supplement or nutrient besides a carbon source may also be fed into the culture in appropriate amounts. The other nutrient or supplement may be monitored and thresholds set appropriately. Supplements such as nitrogen or inorganic phosphate sources are contemplated for use in the present invention. Non-limiting examples of compounds that are contemplated for use in the methods of the present invention include $KH_2PO_4$, $K_2HPO_4$, sodium citrate, dihydrate, $(NH_4)_2SO_4$, $MgSO_4$, $(Na)_2SO_4$, $CaCl_2$, $FeSO_4$, chloramphenicol or any combination thereof. The use of an additional carbon source or sources is also contemplated.

Optical Density and Log Growth Phase:

The introduction of a bacterial host cell to fresh culture media creates a culture that typically goes through four more-or-less distinct phases of growth: (i) lag phase, (ii) log (logarithmic or exponential) phase, (iii) stationary phase, and (iv) decline (death) phase. The log phase itself may be further divided into various phases, such as early log growth phase, mid log growth phase, and late log growth phase. Optical density is related to the phase of log growth. Log growth phase and optical density may also be used as threshold parameters to signal the start and/or stop of the constant feed of the carbon source and/or inducer.

For example, induction, or continuous addition of the inducer may commence at early-log growth phase, mid-log growth phase, and late-log growth phase. Late log growth phase may occur at an OD of about 70 to about 110. In an embodiment of the invention, the constant rate feed of the inducer will start in the late-log growth phase of the culture medium or at an OD of about 70 to about 110, about 70 to about 105, about 75 to about 85, or about 80 in accordance with various embodiments.

OD may be measured at various wavelengths that are commonly employed by those of skill in the art. Typically, $OD_{600}$ is used as a measure of cell growth and density of cells in the culture. Unless otherwise indicated, "OD" as used herein refers to $OD_{600}$.

Dissolved Oxygen:

Another parameter that may serve as a trigger for the start and/or stop of the feed controller is dissolved oxygen (DO) (that is, DO-stat fed batch fermentation). DO may be controlled by adjusting the agitation, airflow, oxygen supplement, and pressure in the vessel to contain the culture media. The threshold of DO may be set in the range from 5% to 80% DO, such as, 20%, 40%, or 80%. Once a threshold has been met, the feed controller for a carbon source or inducer may be turned on until the threshold has been met that signals the stop of the control feed. The stop threshold may be another DO threshold or another parameter, such as the amount of the carbon source or inducer. For example, whenever the DO rises above 30% or 40% in a culture medium, the feed controller may start until which time that the DO falls to 20%, or alternatively, until 0.5 g/L or 1 g/L of a carbon source or inducer has been newly added in accordance with various embodiments of the present invention.

pH:

Another parameter that may serve as a trigger for the start and/or stop of the feed controller is pH (that is, pH-stat fed-batch fermentation). pH may be controlled by addition of base or acid to culture media. The threshold of pH may be set in the range from 6.8 to 7.2, such as 7.0. Once a threshold has been met, the feed controller for a carbon source or inducer may be turned on until the threshold has been met that signals the stop of the control feed. The stop threshold may be another pH threshold or another parameter, such as the amount of the carbon source or inducer. For example, whenever the pH rises to 6.97 in a culture medium, the feed controller may start until which time that the pH falls to 6.95, or alternatively, until 1 g/L of a carbon source or inducer has been newly added in accordance with various embodiments of the present invention.

Harvest Time:

Harvest time represents the amount of time that passes after the initial induction or addition of an inducer. Any suitable harvest time is contemplated by the present invention. Harvest time may range from about 2 hours to about 10 hours, about 2 hours to about 8 hours, about 2.5 hours to about 7 hours, about 3 hours to about 6 hours, etc., in accordance with various embodiments of the present invention. Using the constant feed rate, harvest time, and total amount of inducer, those of ordinary skill in the art will appreciate how each parameter may be adjusted to achieve the desired results. Persons skilled in the art would understand when to harvest based on the amount of arabinose fed because they could readily determine the amount fed based on the feed rate and the time period. In this manner, final concentrations of the inducer of 5, 10, 20, 30, and 40 g/L fed in 3 hours may be achieved, for example, without limitation.

Concentration of the Inducer:

An inducer in any suitable concentration is contemplated by the present invention. Concentrations of the inducer useful to induce host cells may range from about 0.00001% to about 20% (v/v), without limitations.

Temperature:

The culture of the present embodiments may be incubated at any temperature that permits growth of the cells. Various temperatures at which to incubate the culture associated with abundant growth include, without limitation, 22° C., 28° C., 37° C., or any combination thereof.

Fermentation Device

Any suitable fermentation device (that is, "fermentor") is contemplated for use in the present invention, as would be known to persons of skill in the art. For example, the fermentor may contain any number of impellers (such as, Rushton impellers), intakes and/or measurement probes. In accordance with an embodiment, the fermentor is configured to include three Rushton impellers and a ring or tube sparger for introduction of air into the fermentor. The present invention contemplates the use of manual and/or computer-based systems. As such, the fermentation system may interface with a computerized system for monitoring and control of fermentations. In this manner, the system may be fully or partially automated, in accordance with embodiments of the present invention.

Compositions of the Present Invention:

Compositions comprising recombinant proteins, such as those prepared in accordance with the methods of the present invention are provided herein, in accordance with embodiments of the present invention. Compositions of the present invention comprise recombinant protein in high density in a culture, such as the recombinant proteins prepared in accordance with the methods of the present invention, without intending to be limited thereto.

The composition comprises a culture having recombinant protein at a density of at least about 1.5 g/L based on the total volume of the culture. The density of the recombinant protein is at least about 1.7 g/L based on the total volume of the culture according to a further embodiment of the present invention. The density of the recombinant protein is at least about 2.0 g/L based on the total volume of the culture according to another embodiment of the present invention. The density of the recombinant protein is at least about 3.0 g/L based on the total volume of the culture according to another embodiment of the present invention.

A composition comprising recombinant 2086 protein is provided in an embodiment of the present invention. The 2086 protein, as referred to herein, is a protein expressed by a polynucleotide that corresponds to the 2086 gene in *N. meningitidis* serogroup B, including any fragment, derivatives or mutations thereof. Non-limiting exemplary 2086 proteins and polynucleotides are described in WO 03/063766 and WO 04/094596.

The recombinant 2086 protein composition comprises recombinant 2086 protein in a culture wherein the recombinant 2086 protein is at a density of at least about 1.5 g/L based on the total volume of the culture. The density of the recombinant 2086 protein is at least about 1.7 g/L based on the total volume of the culture according to a further embodiment of the present invention. The density of the recombinant 2086 protein is at least about 2.0 g/L based on the total volume of the culture according to another embodiment of the present invention. The density of the recombinant 2086 protein is at least about 3.0 g/L based on the total volume of the culture according to another embodiment of the present invention.

The compositions of the present invention may comprise any protein, such as a protein prepared in accordance with a method of the present invention. The recombinant proteins may be lipidated or nonlipidated proteins. In an embodiment of the invention, the recombinant protein is recombinant 2086 protein either lipidated or non-lipidated. The recombinant 2086 protein may be a 2086 subfamily A or subfamily B protein, or a combination thereof. The compositions of the present invention may include one protein or more than one protein. The proteins may be related or unrelated proteins. For example, a composition of the present invention may include 2086 protein corresponding to one or more strains of subfamily A and/or one or more strains of subfamily B.

Compositions comprising material for use in conducting the methods of the present invention are also provided herein. Such compositions include the necessary components for the culture, including recombinant cells and nutrients, in accordance with embodiments of the present invention. The various compositions may be provided together in a kit, in accordance with an embodiment of the present invention. For example, the components to form the culture may be conveniently pre-packaged in the required amounts to facilitate use in laboratory or industrial settings, without limitation. Such a kit may also include labels, indicia and directions to facilitate the use of each component and the manner of combining the components in accordance with various embodiments of the present invention.

The following examples are included to demonstrate various embodiments of the invention. It should be appreciated by those skilled in the art that the techniques disclosed in the examples which follow represent techniques discovered by the inventors to function well in the practice of the invention, and thus can be considered to constitute various modes for its practice. However, those of skill in the art should, in view of the present disclosure, appreciate that many changes can be made in the specific embodiments which are disclosed and still obtain a like or similar result without departing from the spirit and scope of the invention.

EXAMPLES

Example 1

Fed-Batch Fermentation with Constant Rate Feed

*E. coli* (pPW62) subfamily B was used as a model strain for a fed-batch fermentation process. Based on the results, the process will be applied to the subfamily A *E. coli* (pPW102).

A medium and feed solution for the fed-batch fermentation was prepared using the components as listed in the following tables.

Medium and Feed Solution

TABLE 1

Basal Medium

| Component | Quantity per Liter |
| --- | --- |
| Dextrose, Anhydrous | 10 g |
| $KH_2PO_4$ | 3 g |
| $K_2HPO_4$ | 7 g |
| $(NH_4)_2SO_4$ | 1 g |
| Sodium Citrate, Dihydrate | 1 g |
| $MgSO_4 \cdot 7H_2O$ | 1 g |
| $(Na)_2SO_4$ | 0.58 g |
| $CaCl_2 \cdot 2H_2O$ | 0.075 g |
| $FeSO_4 \cdot 7H_2O$ | 0.09 g |
| 1000x Trace Metal Stock Solution (Table 6) | 1 mL |
| Chloramphenicol | 15 mg |

TABLE 2

1000x Trace Metal Stock Solution

| Component | Quantity per Liter |
| --- | --- |
| $ZnSO_4 \cdot 7H_2O$ | 30 g |
| $CuSO_4 \cdot 5H_2O$ | 9 g |
| $MnSO_4 \cdot H_2O$ | 4.2 g |
| $CoCl_2 \cdot 6H_2O$ | 0.6 g |
| Molybdic Acid, Ammonium Salt, Tetrahydrate | 1.5 g |

TABLE 3

Glucose Concentrate Feed Solution

| Component | Quantity per Liter |
| --- | --- |
| Glucose | 500/700 g |
| $KH_2PO_4$ | 3 g |
| $K_2HPO_4$ | 5 g |
| $(NH_4)_2SO_4$ | 2 g |

TABLE 4

Arabinose Concentrate Feed Solution

| Component | Quantity per Liter |
| --- | --- |
| Arabinose | 250/500 g and varied based on experiment |
| $KH_2PO_4$ | 3 g |
| $K_2HPO_4$ | 5 g |
| $(NH_4)_2SO_4$ | 2 g |

Methods:

Fed-batch fermentation with constant rate feed was used to achieve high cell density in *E. coli* fermentation. The initial glucose concentration was 10 g/L in the medium. The $(NH_4)_2SO_4$ concentration was increased to 3 g/L in the fermentation medium, but held at 1 g/L in the seed culture medium. To determine the feed rate, DO-stat fed-batch was performed first. The DO level was controlled at 20% by a cascade controller that increased the agitation speed to maximum and then used oxygen supplementation. When glucose was depleted, the DO rose sharply (above 40%) and glucose concentrate was added to final concentration of 1 g/L in the fermentor. After each addition of glucose, the pump remained off for a set time before being allowed to make the next addition. The maximum OD of about 160 was achieved when DO-stat fed-batch fermentation was performed. The constant rate was then chosen to be equivalent to the DO-stat controller adding enough glucose to bring the concentration up to 18 g/L or 24 g/L every hour. During the fed-batch fermentation with constant rate feed, the glucose feed was turned on at the desired constant rate when there was a sharp rise to 40% in DO.

The seed cultures were started using one vial of *E. coli* (pPW62) per liter of basal medium+15 μg/mL chloramphenicol in a 2800 mL Fernbach flask. The flasks were incubated at 32° C., 150 rpm overnight (~16 hrs). The final $OD_{600}$ was normally ~3. 10% inoculum size was used to inoculate each fermentor. Each fermentor used 3 Rushton impellers and a ring sparger. Initial setpoints: temp: 36° C., pH: 7.00±0.05 (controlled with 7.4 N $NH_4OH$), airflow: ~1 vvm, DO: 20%. The DO was controlled by a cascade of agitation (min: 150 rpm, max: 1000 rpm) and $O_2$ addition via a gas mix unit. Foam was controlled, if needed, by manual addition of PPG-2000. 0.35 mL/L AF was added to the medium before sterilization. During the fermentation, samples were taken hourly to monitor glucose, pH, and $OD_{600}$ off-line. Supernatants were prepared from 1 mL samples and stored for later analysis of organic acids by HPLC.

Results:

Fed-Batch Fermentation with Constant Rate Feed:

FIG. 1 shows the time courses of OD, glucose consumption, and acetic acid accumulation with constant feed rates. Maximum ODs of 158 and 150 were obtained with constant feed rates of 24 g glucose/L/h and 18 g glucose/L/h, respectively. High glucose 28 g/L was accumulated during the run when a feed rate of 24 g/L/h was used. Glucose accumulates to 12 g/L when a 18 g/L/h feed rate was used. Little acetic acid (that is, less than 1.5 g/L) was produced in both cases. The exponential growth phase ended close to OD 100. The specific growth rate was approximately 0.60 ($hr^{-1}$) in both cases.

Figure 2:
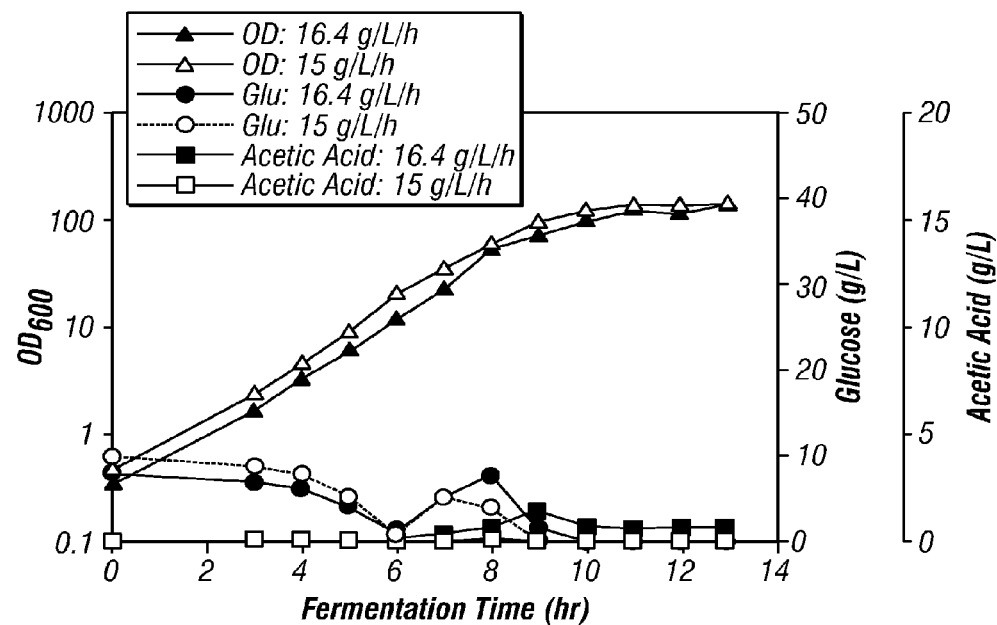

To reduce the glucose accumulation, low constant feed rates of 16.4 g/L/h and 15 g/L/h were examined. FIG. 2 shows the time courses of OD, glucose consumption, and acetic acid accumulation with constant feed rates mentioned above. Maximum ODs were 142 and 147, respectively. As in previous runs, the culture with the faster feed rate accumulated more glucose, although the amount of glucose accumulated was much less than in previous experiments. About 8 g/L of glucose was accumulated during the 16.4 g/L/h, and 5.4 g/L of glucose during the 15 g/L/h fermentation. Little acetic acid (such as less than 1.5 g/L) was produced in both cases (see FIG. 2). The specific growth rate was approximately 0.60 ($hr^{-1}$) in both cases. Thus, the specific growth rate was not affected by the feed rate between 15 g/L/h and 24 g/L/h.

Induction at Various Growth ODs:

A 15 g glucose/LA constant feed rate was used for the arabinose induction study because it resulted in high cell density and low glucose and acetic acid accumulation. In this experiment, inductions at mid-log growth phase OD ~55 and late-log growth phase OD ~80 were compared. The culture was induced by simply substituting the arabinose feed for the glucose feed and feeding arabinose at a constant rate of 13.4 g/Uh. A total of 40 g/L arbinose was added to each culture over the course of 3 hours. After induction, samples were taken every hour for rLP2086 assay by SDS-PAGE, organic acid and arabinose assays by HPLC.

Figure 3:
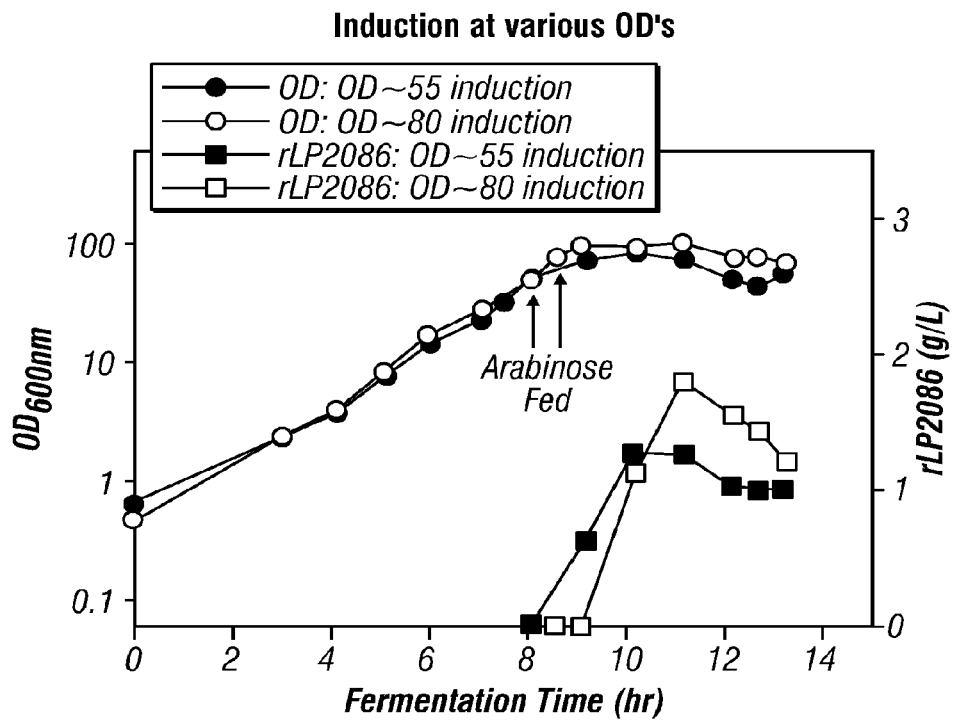

FIG. 3 shows the time courses of OD and rLP2086 production when induced at ODs ~55 and ~80. Both maximum OD and rLP2086 yield were higher when cells were induced at OD ~80 (maximum OD: 101 vs. 84; maximum yield: 1.8 g/L vs. 1.2 g/L).

Induction with Various Arabinose Levels

Figure 4:
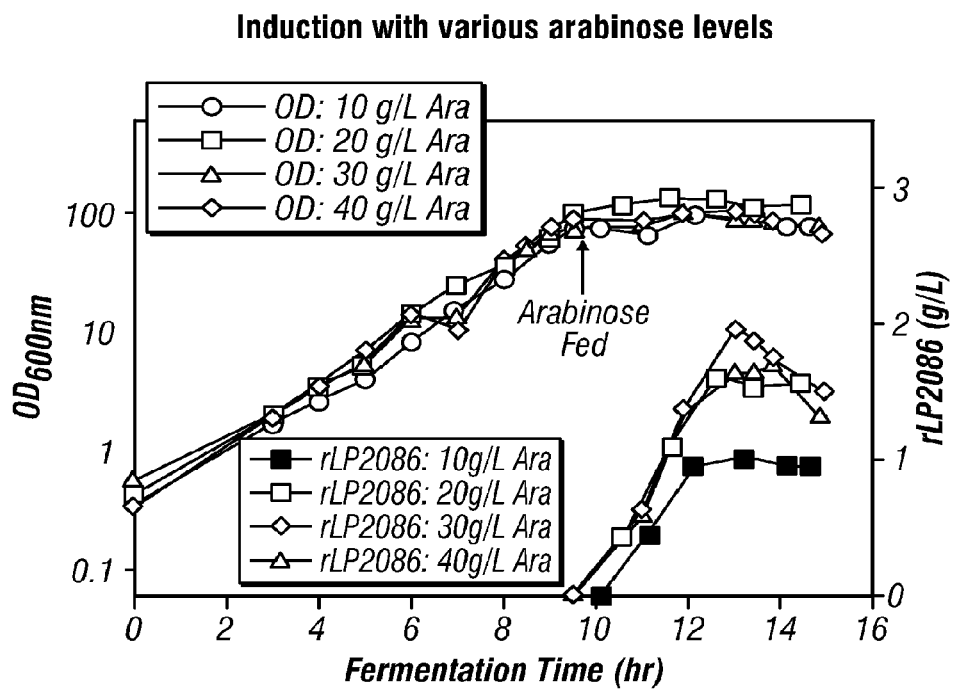

The purpose of the following experiments was to assess the total amount of arabinose fed to the culture and examine whether reduction of the total amount of arabinose fed to the culture would still result in high rLP2086 expression. Arabinose concentrate was fed to 4 different cultures each at different feed rates over the course of 3 hours, resulting in final arabinose concentrations of 10, 20, 30, and 40 g/L. All cultures were induced at $OD_{600}$-80. FIG. 4 shows the time courses of OD and rLP2086 production. Table 5 summarizes the OD and rLP2086 yields for each of the four conditions. It shows the maximum rLP2086 yields of: 1.2 g/L for the g/L total arabinose added; 1.6 g/L for the 20 g/L total arabinose added; 1.7 g/L for the 30 g/L total arabinose added; 2.0 g/L for the 40 g/L total arabinose added. An arabinose feed of between 20 g/L and 40 g/L resulted in similar rLP2086 yield, however, 10 g/L arabinose produced much less rLP2086 (that is, 1.2 g/L). These results suggest that the total amount of arabinose added for induction can be reduced from 40 g/L to 20 g/L without reducing the rLP2086 productivity. Thus, the reduction in arabinose usage would be more cost effective, especially considering the high cost of arabinose (approximately $500/kg US).

TABLE 5

Induction with various arabinose levels

| Lot | Total arabinose fed (g/L) | Maximum rLP2086 (g/L) |
|---|---|---|
| X-BRN05-027 | 10 | 1.2 |
| X-BRN05-024 | 20 | 1.6 |
| X-BRN05-025 | 30 | 1.7 |
| X-BRN10-114 | 40 | 2.0 |

Figure 5:
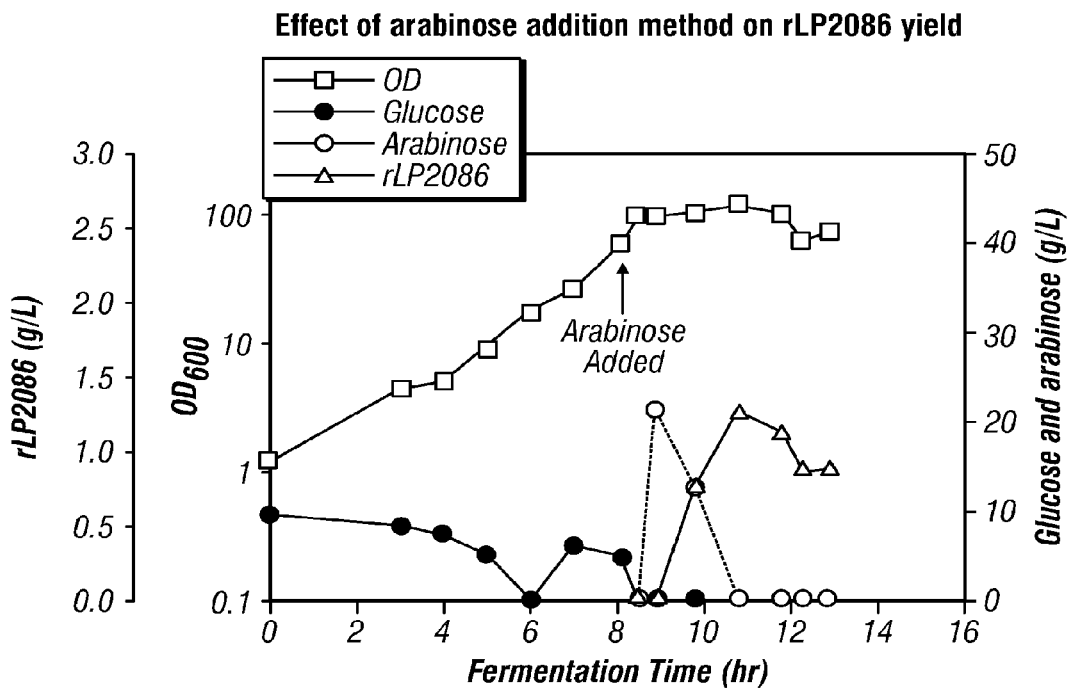

Arabinose Addition Method Comparison:

The following experiment was conducted to examine whether a continuous feeding strategy is superior to a simple batch addition strategy when applied to arabinose for induction. In run X-BRN05-039, 20 g/L of arabinose was added to the fermentor all at once, rather than feeding over the course of time, when the OD was about 80. FIG. 5 shows the time courses of OD, glucose and arabinose consumption, and rLP2086 production. A maximum of 1.3 g/L of rLP2086 was obtained. Batch addition of the arabinose, although operationally simpler, produced less rLP2086 than continuous feeding. Thus, a continuous arabinose feed strategy is superior to simple batch addition.

Figure 6:
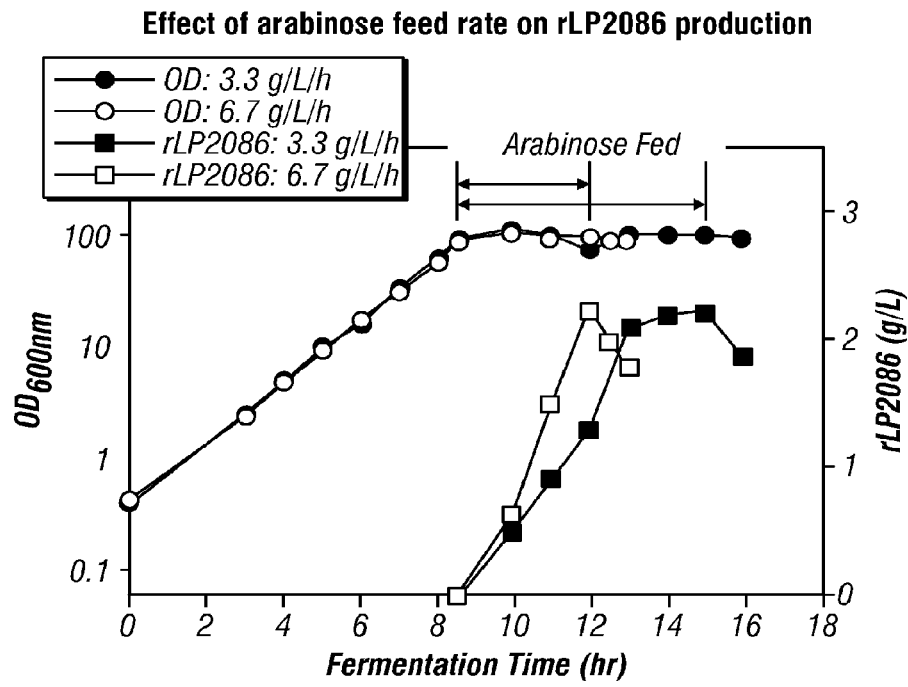

To examine whether the arabinose can be more efficiently used by reducing the arabinose feed rate, feed rates of 3.3 g arabinose/L/h and 6.7 g arabinose/Uh were compared. FIG. 6 shows the time courses of OD and rLP2086 production. Arabinose concentrate was fed to one culture at a feed rate of 6.7 g/Uh over the course of 3 hours, and a second culture was fed at a rate of 3.3 g/Uh over the course of 6 hours. For both cultures, the total amount of arabinose added was 20 g/L. As shown in FIG. 6, both conditions produced the same amount of maximum rLP2086 (that is, 2.2 g/L), but there were differences in the kinetics of the production. The higher feed rate resulted in a higher production rate. Maximum rLP2086 was achieved at 3 hours and 6 hours after induction with feed rates of 6.7 g/Uh and 3.3 g/Uh, respectively. The advantage of using a higher feed rate (that is, 6.7 g/Uh) is that production cost (for example, utility cost) will be lower when using a higher feed rate than when using a lower feed rate.

Effect of Induction Time on rLP2086 Expression Yield

Figure 7:
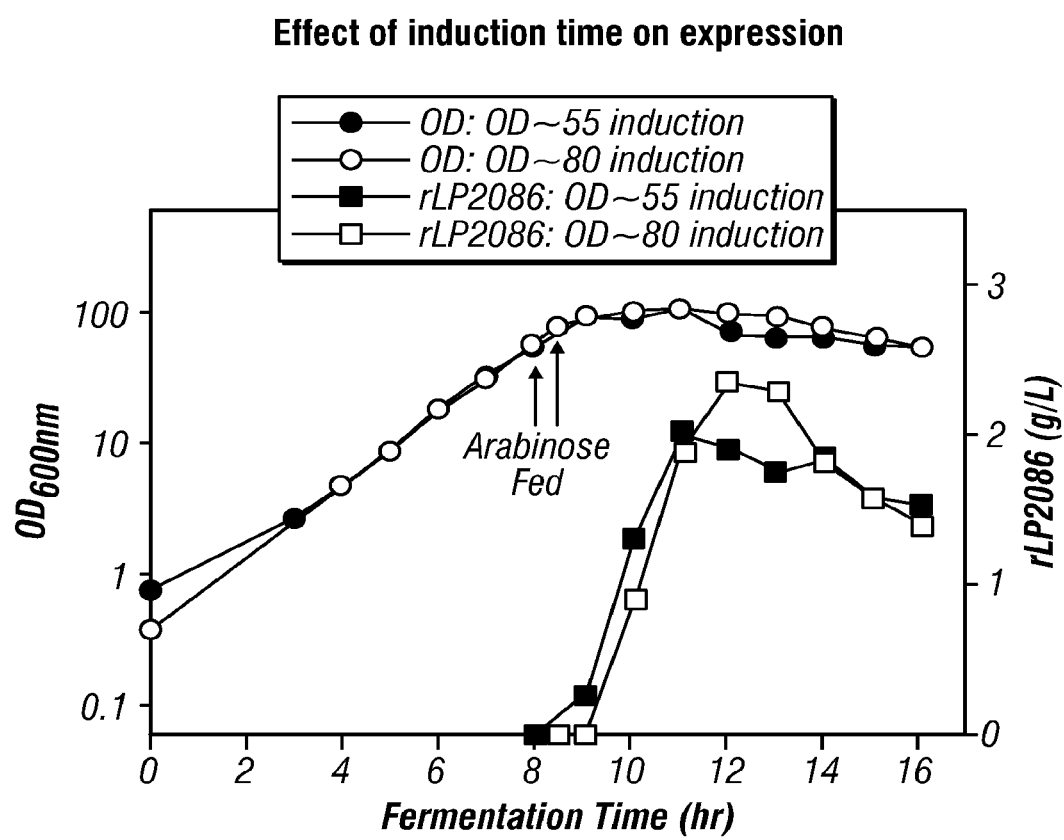

To determine the optimum harvest time, the normal feeding profile (20 g/L arabinose fed over 3 hours) was extended to 40 g/L fed over 6 hours. In runs X-BRN05-028 and X-BRN05-029, the cells were induced at OD ~55 and OD ~80, respectively. FIG. 7 shows the time courses of OD and rLP2086 production. Although the arabinose feed extended from 3 hours to 6 hours, interestingly, the peak titer was still obtained around 3 hours after induction. The product titer was slightly higher in the culture that was induced at higher OD. The maximum rLP2086 yield at induction OD ~55 was 2.0 g/L (X-BRN05-028) while it was 2.4 g/L at induction OD-80 (X-BRN05-029). This result suggests that the cells should be harvested 3 hours after induction.

Comparison of Feed Solution with and without Salts

To examine whether added salts are essential in the glucose and arabinose feed solutions, plain glucose and arabinose feeds were compared with the standard glucose+salts (that is, $K_2HPO_4/KH_2PO_4+(NH_4)_2SO_4$) and arabinose+salts feeds. For both cultures, 20 g/L of arabinose was fed over the course of 3 hours. The growth and rLP2086 production profiles were very similar. The maximum rLP2086 yield was 1.8 g/L when salts were added to the feeds, and 2.0 g/L when glucose and arabinose feeds were prepared without salts. These results suggest that there is no need to add salts to the glucose and arabinose feed solutions.

Figure 8:
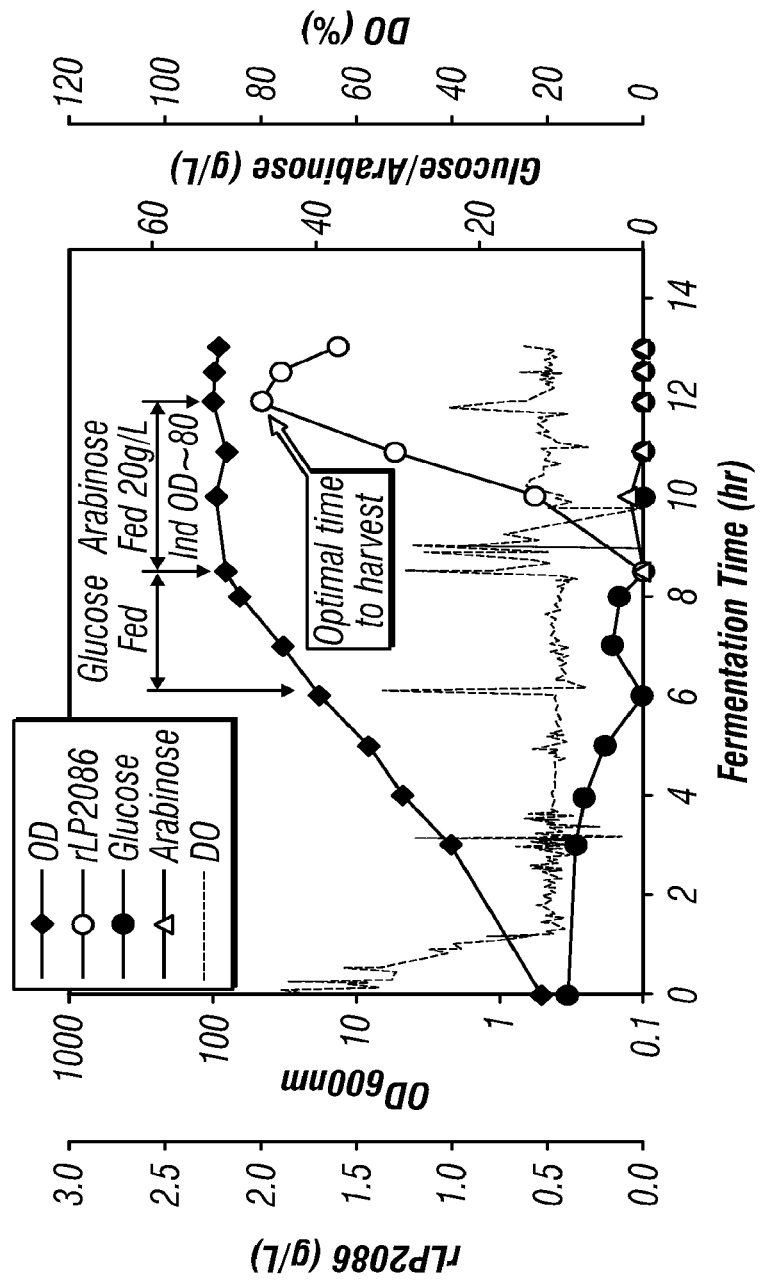
Figures 9A, 9B:
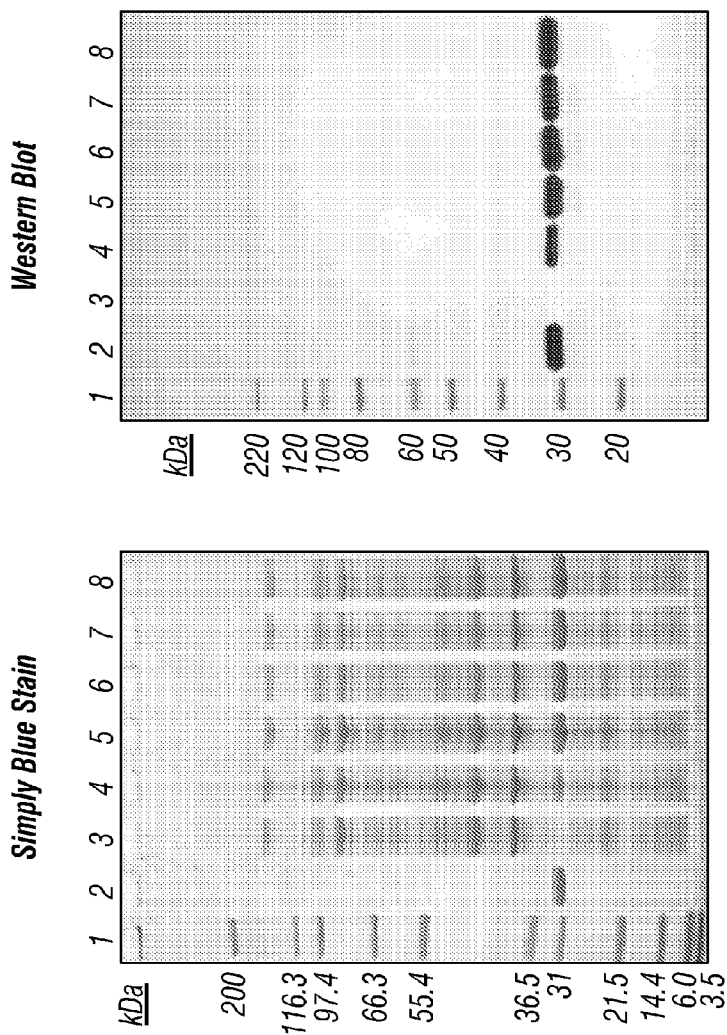

Fed-Batch Fermentation with Constant Rate Feed for Subfamily B Strain:

Seed cultures were started by inoculating 1 L of basal medium containing 15 μg/mL chloramphenicol with 1 ml of thawed working seed. The culture was grown in a 2.8 L Fernbach flask and was incubated for about 16 hours at 32° C. and 150 rpm. The final $OD_{600}$ was ~3.0. 350 mL seed cultures were aseptically transferred into 3.15 L basal medium containing 3 g/L $(NH_4)_2SO_4$ without chloramphenicol. The fermentation was controlled at pH 7.0±0.05 by 7.4 N $NH_4OH$, temperature at 36° C., DO at 20%, and airflow at 1 vvm. The DO was controlled by a cascade of agitation (min: 150 rpm, max: 1000 rpm) and oxygen addition. Antifoam PPG-2000 was automatically added to control foam. During the fermentation, samples were taken hourly to monitor glucose and OD off-line. After inoculation, the DO dropped from ~100% to 20% and then was maintained at 20%. When there was a sharp rise in DO from 20% to greater than 40% (usually 6 hours Elapsed Fermentation Time (EFT)), the glucose (without salts) feed pump was turned on at a rate of 15 g/L/h. As shown in FIG. 8, glucose was completely depleted by 6-hour EFT, resulting in a sharp rise in the DO. The samples were taken every half hour when OD reached ~40. The glucose feed was turned off at OD 90 and the arabinose feed was turned on at a rate of 13.4 g/L/h. After 3 hours of arabinose (without salts) feeding (that is, a total 20 g/L arabinose addition), the arabinose feed was turned off and the fermentation was allowed to continue for another hour. As shown in FIG. 8, an OD of 102 was obtained and 2.0 g/L of MnB rLP2086 was expressed based on SDS-PAGE (see FIG. 9). The peak occurred 3 hours after induction (that is, ~12-hour EFT). SDS-PAGE and Western Blot showed that the expressed protein was indeed subfamily B rLP2086.

Figure 10:
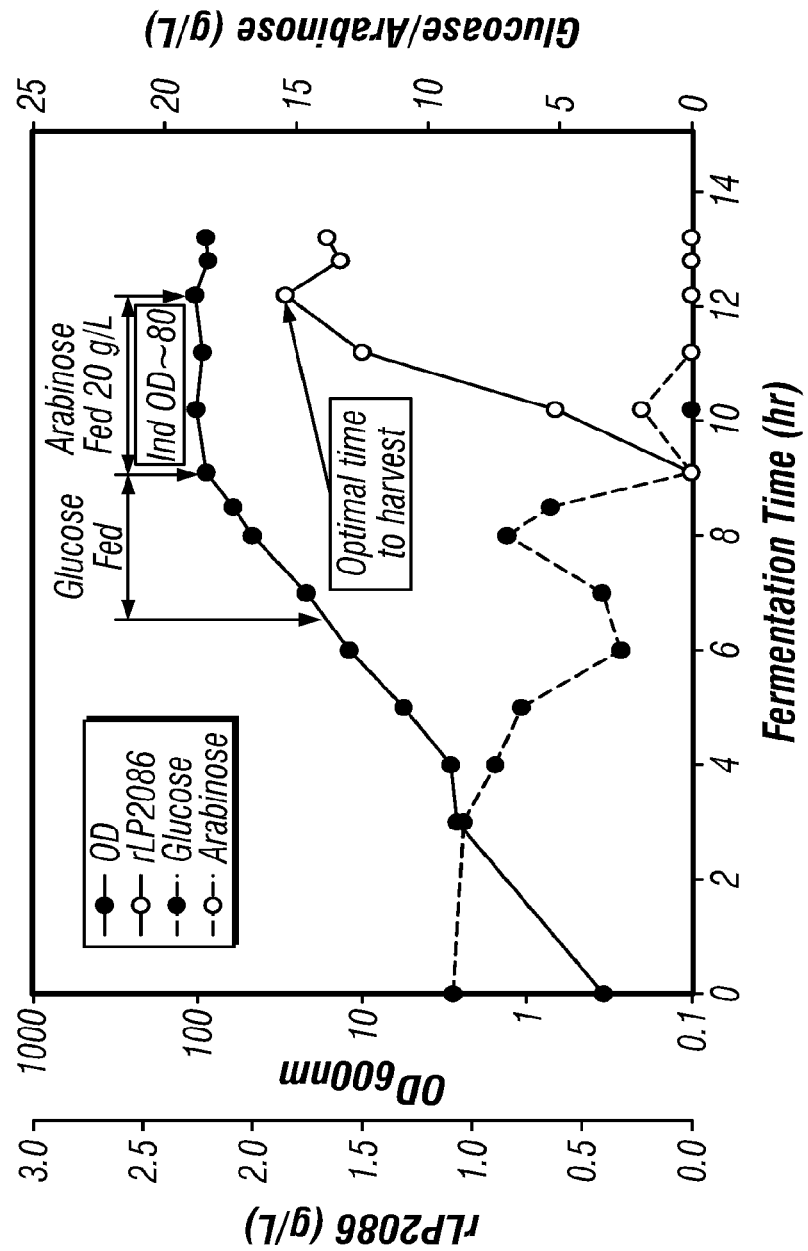
Figures 11A, 11B:
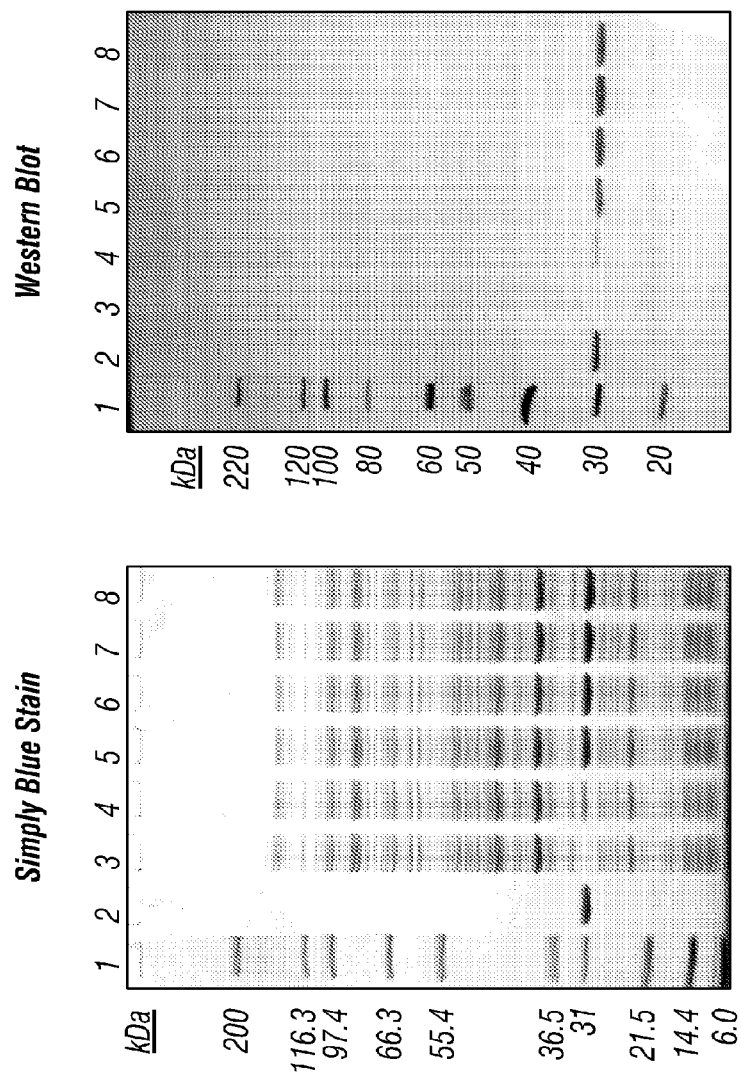

Application of Fed-Batch Fermentation Process for MnB rLP2086 Subfamily a Strain:

To test whether the fed-batch fermentation process used for rLP2086 subfamily B was applicable to rLP2086 subfamily A, the process was conducted using the procedure established for the subfamily B strain. FIG. 10 shows the time courses of OD, glucose and arabinose consumption, and rLP2086 production. The growth and rLP2086 production profiles for subfamily A were similar to those obtained for subfamily B (compare to FIG. 8). SDS-PAGE and Western Blot showed that expressed protein was indeed subfamily A rLP2086 (see FIG. 11). Table 6 lists the maximum ODs and rLP2086 expression yields for six different subfamily A runs. The range of maximum rLP2086 expression yield was 1.5-2.1 g/L (average maximum yield: 1.8±0.2 g/L), similar to the results from the fed-batch fermentations used to produce rLP2086 subfamily B. Thus, the fed-batch fermentation developed for subfamily B strain is also suitable for subfamily A strain.

TABLE 6

Maximum subfamily A rLP2086 expression yield and OD

| Lot | Maximum rLP2086 (g/L) | Maximum OD |
|---|---|---|
| X-BRN10-118 | 1.9 | 104 |
| X-BRN10-119 | 1.9 | 104 |
| X-BRN10-120 | 1.6 | 100 |
| X-BRN05-042 | 1.5 | 100 |
| X-BRN05-043 | 2.0 | 77 |
| X-BRN10-121 | 2.1 | 92 |

Dual Glucose and Arabinose Feed During the Arabinose Induction

To reduce the amount of arabinose needed without reducing rLP2086 production, dual glucose and arabinose feed during the induction period was investigated. The strategy was to feed 10 g/L of arabinose over 3 hrs (half the usual amount) while continuing to feed glucose during the induction phase at 25% (3.75 g/L/h), 50% (7.5 g/L/h), and 100% (15 g/L/h) of the standard glucose feed rate. All of the feeds, glucose and arabinose, were prepared without additives.

Figure 12A:
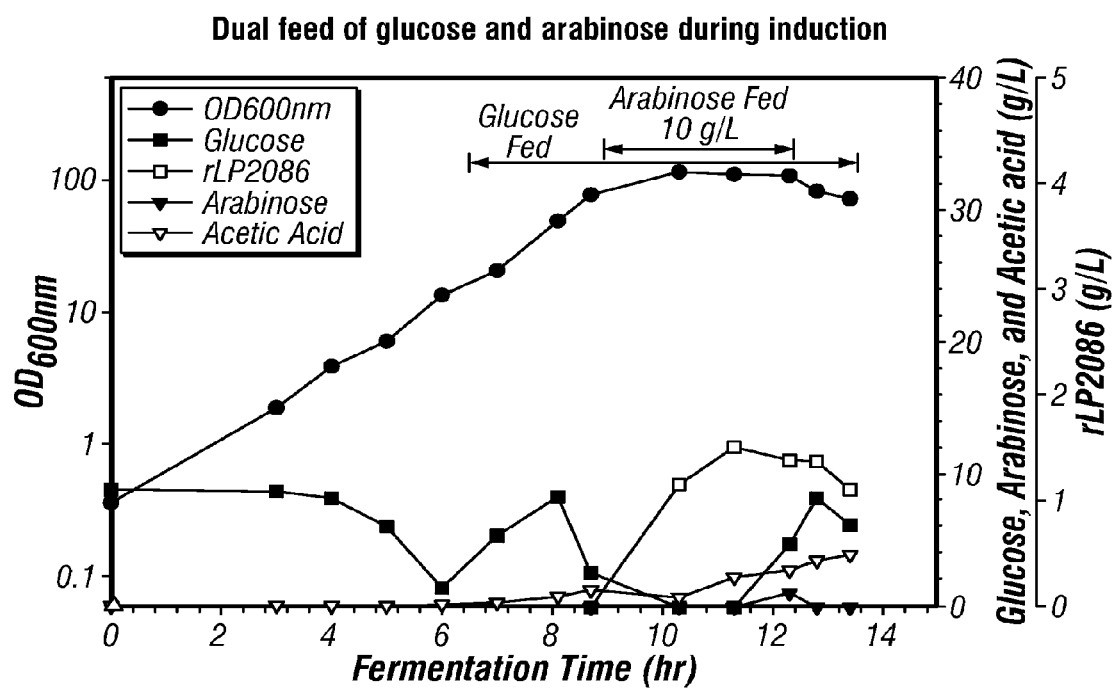
Figure 12B:
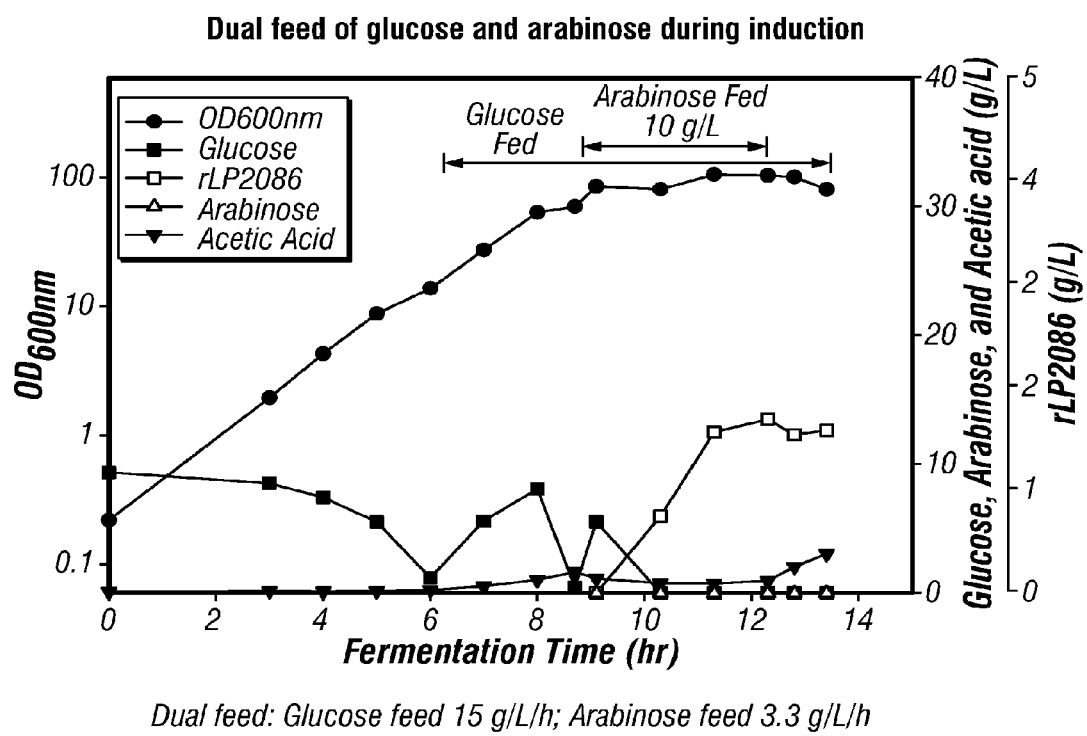
Figure 12C:
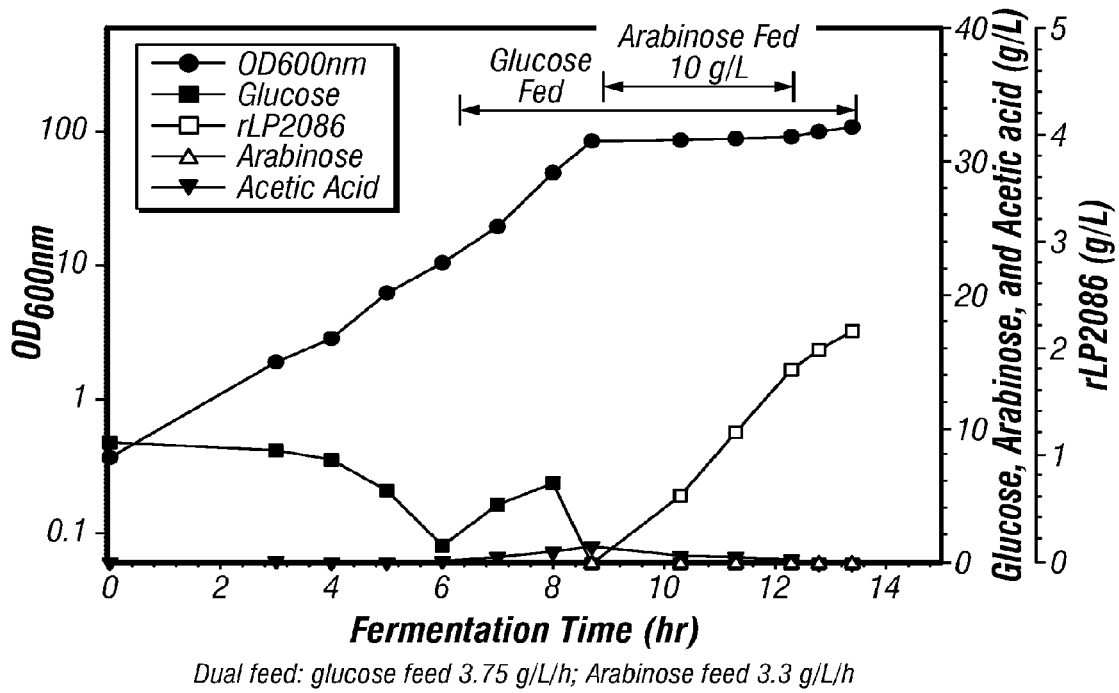

FIGS. 12a, 12b, and 12c, show the time course of subfamily B cell growth, the glucose, arabinose, acetic acid concentrations, and rLP2086 production. All three runs were induced at OD ~80. As shown in FIG. 12a, the OD of the 100% glucose feed run continued to rise after induction, peaking at 117, while the 50% run peaked at 106 (FIG. 12b) and the 25% run held around 100 (FIG. 12c) after induction. The 100% glucose feed began to accumulate glucose and arabinose by 3 hours post-induction. The 50% glucose run only showed a slight amount of glucose in the last sample (reading=0.21 g/L). There was no glucose accumulation in the 25% glucose run. None of three runs accumulated any arabinose. The 100% (FIG. 12a) and 50% (FIG. 12b) glucose fed runs produced ~1.5 and 1.7 g/L rLP2086, respectively, while the 25% (FIG. 12c) run produced over 2.1 g/L. The 100% runs' production peaked before the arabinose ran out, suggesting that rLP2086 expression may have been suppressed by the accumulation of glucose and acetic acid. The 50% runs' production peaked about the time the arabinose ran out and the 25% runs' production peaked after the arabinose ran out suggesting that 2086 expression might not be suppressed as long as glucose concentration was controlled at minimal level (no glucose accumulated in FIGS. 12b and 12c). Although only 10 g/L of arabinose was fed to these cultures, their rLP2086 production was similar to that obtained when 20 g/L was fed. Simultaneous feeds of glucose and arabinose can reduce the arabinose consumption by 50% and still achieve the same rLP2086 yield when glucose concentration is controlled at a low level during the induction. Thus, the cost of chemicals can be reduced significantly.

To examine whether one can further reduce arabinose consumption and increase rLP2086 yield, various glucose feed rates, total amounts of arabinose fed, and induction ODs were investigated. Table 7 lists different combinations of these conditions. It appears that glucose feed rate between 2.25 and 7.5 g/L/h and arabinose feed rate between 1.7 and 6.7 g/L/h would not affect rLP2086 yield significantly. Induction ODs between 80 and 105 result in similar rLP2086 yield.

TABLE 7

Maximum OD and rLP2086 under different glucose feed rate, different amount of arabinose addition, and induction at various OD

| Lot number | Glucose feed rate (g/L/h) | Arabinose feed rate (g/L/h) | Amount of arabinose fed | Induction OD | Maximum OD | Maximum rLP2086 (g/L) |
|---|---|---|---|---|---|---|
| X-BRN10-127 | 3.75 | 1.7 | 5 g/L in 3 hours | 74 | 86 | 1.6 |
| X-BRN05-056 | 3.75 | 3.3 | 20 g/L in 3 hours | 79 | 122 | 2.8 |
| X-BRN05-058 | 3.75 | 1.7 | 10. g/L in 6 hours | 94 | 122 | 3.0 |
| X-BRN10-129 | 3.75 | 6.7 | 20. g/L in 3 hours | 110 | 124 | 2.7 |
| X-BRN05-059 | 3.75 | 3.3 | 20. g/L in 6 hours | 105 | 126 | 2.9 |
| X-BRN05-061 | 5.25 | 3.3 | 20. g/L in 6 hours | 102 | 112 | 2.6 |
| X-BRN10-130 | 2.25 | 3.3 | 20. g/L in 6 hours | 93 | 108 | 2.4 |

Example 3

Scaled-Up Fed-Batch Fermentation to 100 L Scale

The seed culture was started by inoculating 2×1 L basal medium containing 15 μg/mL chloramphenicol with 1 ml (that is, 1 vial) of thawed working seed. The culture in 2.8 L Fernbach was incubated for about 16 hours at 32° C. and 150 rpm in a rotary shaker.

Two 1 L overnight Fernbach seed cultures were aseptically transferred into a 150 L fermentor containing 70 L basal medium without chloramphenicol. The 150 L fermentation in basal medium was controlled at pH 7.0±0.05 by 7.4 N $NH_4OH$, temperature 36° C., DO 20%, and air flow at 1 vvm. The DO was controlled by a cascade of agitation and oxygen addition. Antifoam PPG-2000 was automatically added to control foam. During the fermentation, the DO dropped from ~100% to 20% and was maintained at 20%. When there was a sharp rise in DO from 20% to greater than 40% (usually at OD ~20), signaling the depletion of glucose, the feed pump was activated to deliver the glucose concentrate (that is, 500 g/L) at a rate of 15 g glucose/L broth/h. During the fermentation, samples were taken hourly to monitor glucose and OD off-line. The samples were taken every half hour when OD reached ~40. Once OD reached ~80, the glucose feed was stopped and the arabinose feed was started (for example, 500 g/L of arabinose concentrate) at a rate of 6.7 g arabinose/L broth/h for 3 hours.

Figure 13A:
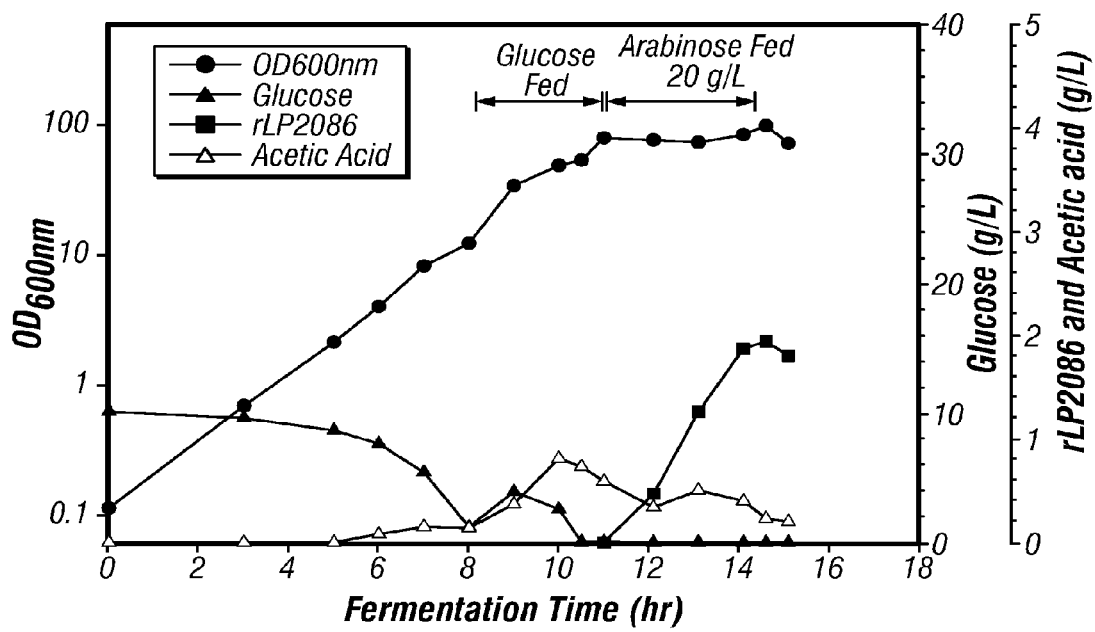

FIG. 13a shows the time courses of subfamily B cell growth, the glucose consumption, acetic acid accumulation, and rLP2086 production at 100 L scale. The fermentation profile at the 100 L scale was similar to that seen at the small-scale. A maximum OD of 99 and a maximum yield of 1.9 g/L rLP2086 were obtained. These results demonstrate that the fed-batch fermentation is scalable.

Figure 13B:
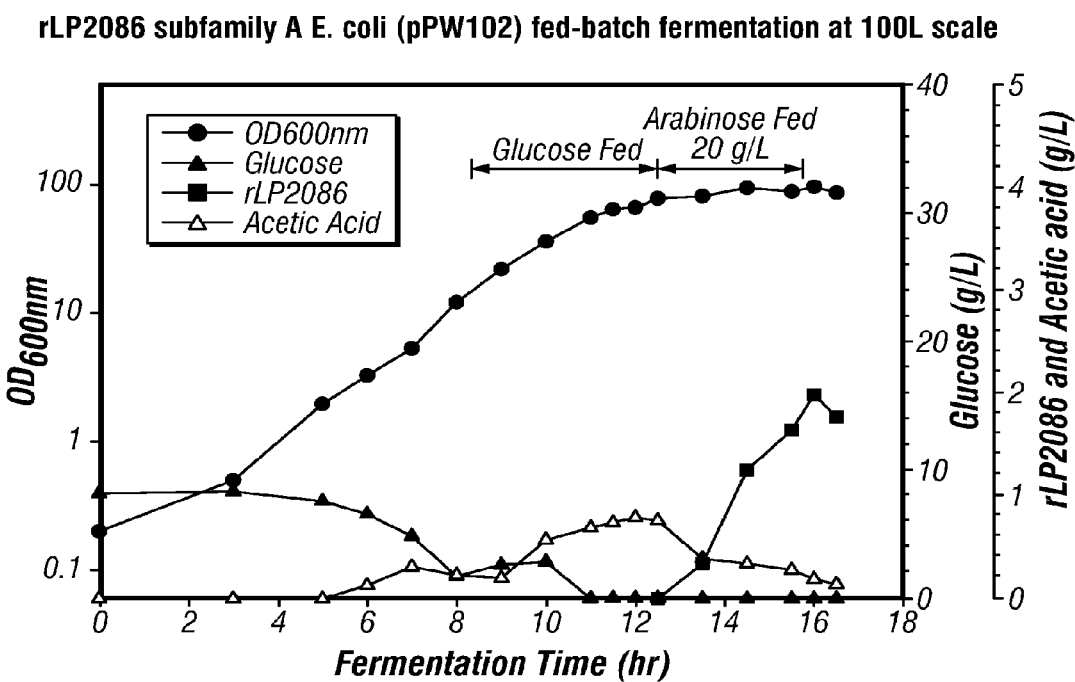

FIG. 13b shows the time courses of subfamily A cell growth, the glucose consumption, acetic acid accumulation, and rLP2086 production at the 100 L scale. The fermentation profile at 100 L scale was similar to that seen at the small-scale. A maximum OD of 96 and a maximum yield of 2.0 g/L rLP2086 were obtained. These results demonstrate that the fed-batch fermentation is scalable and robust.

Figure 14A:
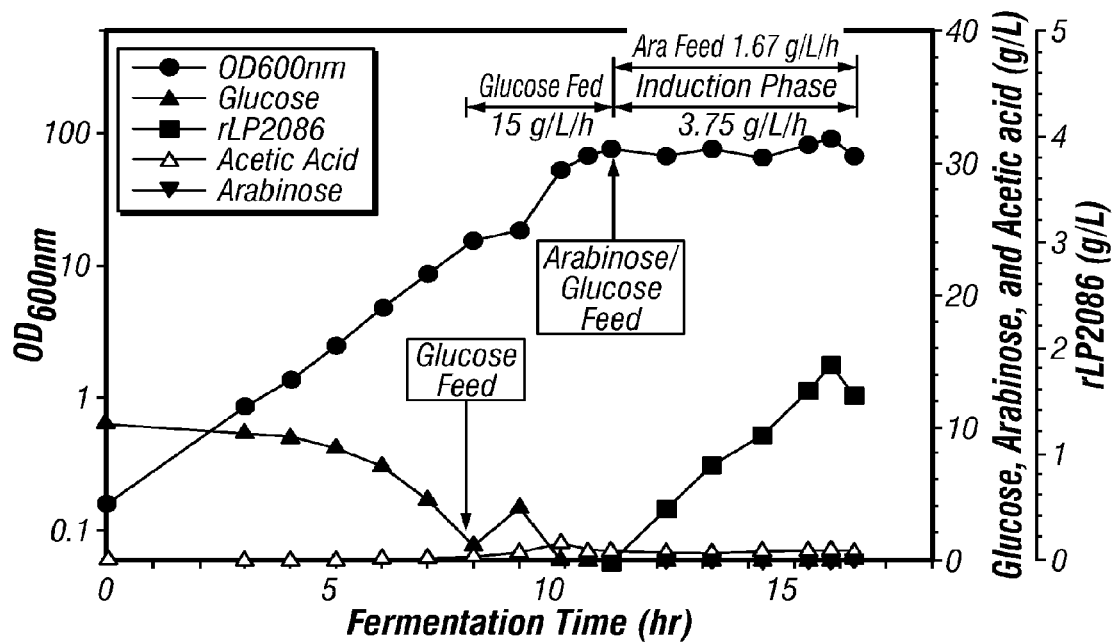

FIG. 14a shows the time courses of subfamily B cell density, glucose, arabinose, acetic acid concentrations, and rLP2086 yield with dual glucose and arabinose feed at 100 L scale. During the induction, feed rates were controlled at 3.75 and 1.67 g/L/h for glucose and arabinose feeding, respectively. Dual arabinose and glucose was fed in 5 hours. A maximum OD of 90 and a maximum yield of 1.8 g/L rLP2086 were obtained. The maximum rLP2086 yield appeared at 4-hour induction. Average maximum OD and average maximum rLP2086 yield for subfamily B were 84.8±6.8 and 1.6±0.3 g/L, respectively. These results demonstrate that the fed-batch fermentation with dual glucose and arabinose feed during the induction phase is scalable.

Figure 14B:
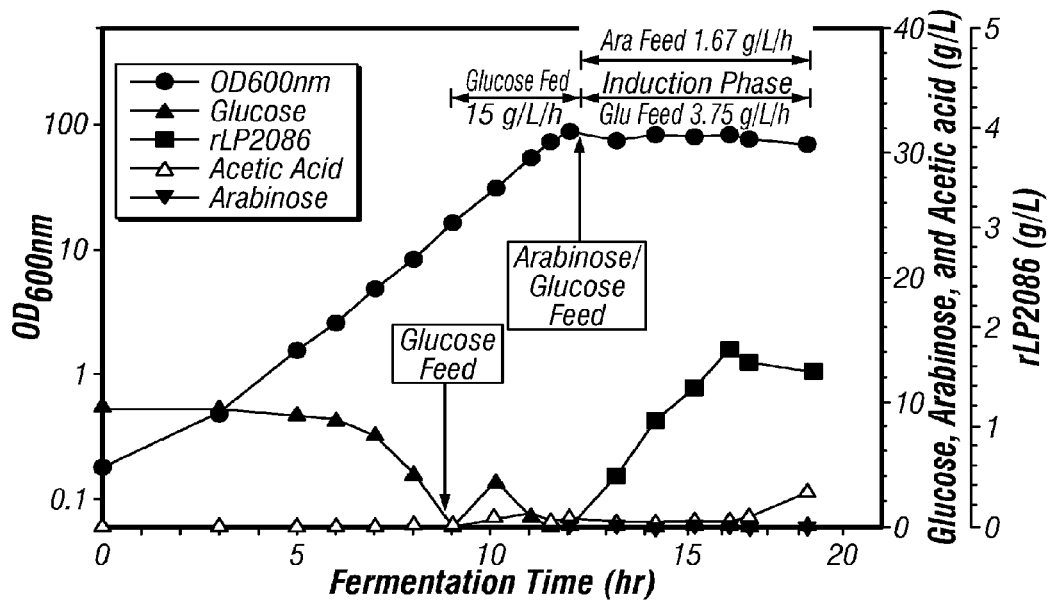

FIG. 14b shows the time courses of subfamily A cell growth, the glucose consumption, acetic acid accumulation, and rLP2086 production at the 100 L scale. The fermentation ran at the same conditions as in the immediately preceding paragraph and cells were induced for 6 hours. A maximum OD of 89 and a maximum yield of 1.8 g/L rLP2086 were obtained. The maximum rLP2086 yield appeared at 4-hour induction. Average maximum OD is 87.9±10.5 and average maximum rLP2086 yield is 1.8±0.2 g/L for subfamily A. These results demonstrate that the fed-batch fermentation is scalable and robust.

While the invention has been described with reference to various embodiments and examples, those skilled in the art recognize that various modifications may be made to the invention without departing from the spirit and scope thereof.

The invention claimed is:

1. A method for producing a recombinant protein comprising culturing a recombinant bacterial cell to express a recombinant protein in a culture; continuously adding a carbon source to the culture; continuously adding arabinose to the culture after the culture achieves a threshold parameter, said arabinose being added to the culture simultaneously to the continuous addition of the carbon source; and isolating the recombinant protein from the culture, wherein the carbon source feed rate during the arabinose induction is between 2.25 and 7.5 g/L/h; and wherein the arabinose feed rate is between 1.7 and 6.7 g/L/h.

2. The method of claim 1, wherein the threshold parameter is optical density (OD), dissolved oxygen (DO), concentration of nutrient in culture medium, total concentration of carbon source added to culture medium, or any combination thereof.

3. The method of claim 2, wherein the threshold parameter is optical density (OD) of the culture.

4. The method of claim 3, comprising continuously adding the arabinose to the culture when the cell density of the culture achieves an $OD_{600}$ of about 70 to about 110.

5. The method of claim 4, comprising continuously adding the arabinose to the culture when the cell density of the culture achieves an $OD_{600}$ of about 70 to about 105.

6. The method of claim 5, comprising continuously adding the arabinose to the culture when the cell density of the culture achieves an $OD_{600}$ of about 70 to about 85.

7. The method of claim 6, comprising continuously adding the arabinose to the culture when cell density of the culture achieves an $OD_{600}$ of about 80.

8. The method of claim 1, comprising adding the arabinose to the culture at a constant rate, adding the arabinose to the culture by DO-stat feed or adding the arabinose to the culture by pH-stat feed.

9. The method of claim 1, wherein the arabinose feed rate is about 1.7 g/L/h.

10. The method of claim 1, comprising continuously adding arabinose to the culture for 2 to 8 hours after initiation of the method.

11. The method of claim 10, comprising continuously adding arabinose to the culture for 3 to 6 hours after initiation.

12. The method of claim 1, comprising continuously adding arabinose to the culture about 3 hours after initiation.

13. The method of claim 1, wherein the arabinose feed rate is about 1.7 g/L/h.

14. The method of claim 1, comprising continuously adding the carbon source to the culture before induction.

15. The method of claim 14, wherein the carbon source feed rate before induction is between 1.5 to 24 g/L/h.

16. The method of claim 15, wherein the carbon source feed rate before induction is about 18 g/L/h.

17. The method of claim 1, comprising continuously adding the carbon source to the culture before and during induction.

18. The method of claim 1, comprising continuously adding the carbon source to the culture while the arabinose is continuously added to the culture.

19. The method of claim 1, comprising continuously adding the carbon source to the culture until the cell density of the culture achieves an $OD_{600}$ of about 70 to about 110.

20. The method of claim 1, wherein carbon source is fed to the culture at a constant feed rate during the constant rate feed of arabinose to the culture, by DO-stat feed of both the glucose and the arabinose until the cell density in the culture achieves an $OD_{600}$ of about 80 or by pH-stat feed of both the glucose and the arabinose until the cell density in the culture achieves an $OD_{600}$ of about 80.

21. The method of claim 1, wherein the carbon source is a sugar-based carbon source.

22. The method of claim 20, wherein the sugar-based carbon source is glucose.

23. The method of claim 22, comprising continuously adding the glucose to the culture medium while the arabinose is continuously added to the culture medium.

24. The method of claim 22, comprising continuously adding the glucose until the cell density of the culture achieves an $OD_{600}$ of about 80.

25. The method of claim 1, wherein the bacterial cell comprises a nucleic acid sequence encoding a gene of *Neisseria meningitidis* serogroup B.

26. The method of claim 1, wherein the recombinant protein is a meningococcal protein.

27. The method of claim 26, wherein the meningococcal protein is a meningococcal 2086 protein.

28. The method of claim 26, wherein the protein is lipidated.

29. The method of claim 26, wherein the protein is non-lipidated.

30. The method of claim 26, wherein the protein comprises a meningococcal 2086 subfamily A protein.

31. The method of claim 26, wherein the protein comprises a meningococcal 2086 subfamily B protein.

32. The method of claim 1, wherein the recombinant bacterial cell is derived from *E. coli*.

33. The method of claim 1, wherein the recombinant bacterial cell further comprises an expression vector encoding the recombinant protein, said vector comprising an arabinose promoter.

* * * * *